United States Patent
Retsch, Jr. et al.

(10) Patent No.: US 11,286,401 B2
(45) Date of Patent: *Mar. 29, 2022

(54) COATING COMPOSITION COMPRISING A THERMOSET RESIN AND A THERMOPLASTIC RESIN

(71) Applicant: PPG Industries Ohio, Inc., Cleveland, OH (US)

(72) Inventors: William H. Retsch, Jr., Allison Park, PA (US); Anthony M. Chasser, Greensburg, PA (US); Edward R. Millero, Jr., Gibsonia, PA (US); John M. Dudik, Apollo, PA (US)

(73) Assignee: PPG Industries Ohio, Inc., Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/086,973

(22) Filed: Nov. 2, 2020

(65) Prior Publication Data

US 2021/0147709 A1 May 20, 2021

Related U.S. Application Data

(63) Continuation of application No. 16/069,587, filed as application No. PCT/IB2017/050188 on Jan. 13, 2017, now Pat. No. 10,858,536, which is a continuation of application No. 15/151,547, filed on May 11, 2016, now abandoned, and a continuation of application No. 14/996,838, filed on Jan. 15, 2016, now abandoned.

(30) Foreign Application Priority Data

Jan. 15, 2016 (EP) ..................... 16151619
Jan. 15, 2016 (EP) ..................... 16151620
Jan. 15, 2016 (EP) ..................... 16151621

(51) Int. Cl.
| | |
|---|---|
| *C09D 175/12* | (2006.01) |
| *B27N 7/00* | (2006.01) |
| *B65D 1/12* | (2006.01) |
| *C07C 275/14* | (2006.01) |
| *C07C 275/26* | (2006.01) |
| *C08G 18/24* | (2006.01) |
| *C08G 18/32* | (2006.01) |
| *C08G 18/34* | (2006.01) |
| *C08G 18/48* | (2006.01) |
| *C08G 18/66* | (2006.01) |
| *C08G 18/67* | (2006.01) |
| *C08G 18/73* | (2006.01) |
| *C08G 18/75* | (2006.01) |
| *C08G 18/79* | (2006.01) |
| *C08G 18/80* | (2006.01) |
| *C09D 5/02* | (2006.01) |
| *C09D 5/03* | (2006.01) |
| *C09D 175/02* | (2006.01) |
| *C09D 175/16* | (2006.01) |
| *B27N 3/00* | (2006.01) |

(52) U.S. Cl.
CPC .......... *C09D 175/12* (2013.01); *B27N 7/005* (2013.01); *B65D 1/12* (2013.01); *C07C 275/14* (2013.01); *C07C 275/26* (2013.01); *C08G 18/246* (2013.01); *C08G 18/3275* (2013.01); *C08G 18/348* (2013.01); *C08G 18/48* (2013.01); *C08G 18/4854* (2013.01); *C08G 18/6692* (2013.01); *C08G 18/672* (2013.01); *C08G 18/73* (2013.01); *C08G 18/751* (2013.01); *C08G 18/755* (2013.01); *C08G 18/792* (2013.01); *C08G 18/8041* (2013.01); *C09D 5/02* (2013.01); *C09D 5/03* (2013.01); *C09D 175/02* (2013.01); *C09D 175/16* (2013.01); *B27N 3/002* (2013.01)

(58) Field of Classification Search
CPC .......... C09D 175/12; C09D 5/02; C09D 5/03; C09D 175/02; C09D 175/16; B27N 7/005; B27N 3/002; B65D 1/12; C07C 275/14; C07C 275/26; C08G 18/246; C08G 18/3275; C08G 18/348; C08G 18/48; C08G 18/4854; C08G 18/6692; C08G 18/672; C08G 18/73; C08G 18/751; C08G 18/755; C08G 18/792; C08G 18/8041

See application file for complete search history.

(56) References Cited

U.S. PATENT DOCUMENTS

| | | |
|---|---|---|
| 3,294,751 A | 12/1966 | Beitchman |
| 3,420,787 A | 1/1969 | Reymore et al. |

(Continued)

FOREIGN PATENT DOCUMENTS

| | | |
|---|---|---|
| CN | 1662618 A | 8/2005 |
| CN | 101098935 A | 1/2008 |

(Continued)

OTHER PUBLICATIONS

Machine English translation of CN101098935.

(Continued)

*Primary Examiner* — Michael C Miggins
(74) *Attorney, Agent, or Firm* — Michael J. Grese

(57) ABSTRACT

A powder coating composition comprising:
a) a thermoset resin comprising an acid functional polyester material,
b) a thermoplastic resin and
c) a crosslinker material,
wherein the coating composition is substantially free of bisphenol A (BPA), bisphenol F (BPF), bisphenol A diglycidyl ether (BADGE) and bisphenol F diglycidyl ether (BFDGE).

22 Claims, No Drawings

(56) References Cited

U.S. PATENT DOCUMENTS

| | | | |
|---|---|---|---|
| 3,663,516 A | | 5/1972 | Vogt |
| 3,867,480 A | * | 2/1975 | Fujiyoshi .............. C08G 63/12 |
| | | | 525/172 |
| 3,972,844 A | * | 8/1976 | Morosawa ............. C09D 5/032 |
| | | | 524/37 |
| 4,211,683 A | | 7/1980 | Wenzel |
| 4,284,572 A | | 8/1981 | Stanley et al. |
| 4,990,579 A | | 5/1991 | Paar |
| 5,030,754 A | | 7/1991 | Speranza et al. |
| 5,047,294 A | | 9/1991 | Schwab et al. |
| 5,574,083 A | | 11/1996 | Brown et al. |
| 5,714,539 A | | 2/1998 | Perez et al. |
| 5,858,549 A | | 1/1999 | Kielbania, Jr. et al. |
| 5,898,043 A | * | 4/1999 | Uemae .................. C09D 5/031 |
| | | | 523/204 |
| 5,965,466 A | | 10/1999 | Rodrigues et al. |
| 6,051,646 A | | 4/2000 | Nass et al. |
| 6,140,388 A | | 10/2000 | Nass et al. |
| 6,181,311 B1 | | 1/2001 | Hashimoto |
| 6,248,819 B1 | | 6/2001 | Masuda et al. |
| 6,290,867 B1 | | 9/2001 | Kielbania, Jr. et al. |
| 6,875,800 B2 | | 4/2005 | Vanier et al. |
| 6,894,086 B2 | | 5/2005 | Munro et al. |
| 7,033,526 B2 | | 4/2006 | Figiel et al. |
| 7,605,194 B2 | | 10/2009 | Ferencz et al. |
| 8,153,344 B2 | | 4/2012 | Faler et al. |
| 8,846,156 B2 | | 9/2014 | Swarup et al. |
| 2004/0266921 A1 | | 12/2004 | Rodrigues et al. |
| 2005/0113269 A1 | | 5/2005 | Landa et al. |
| 2005/0171300 A1 | | 8/2005 | Moens |
| 2008/0004361 A1 | | 1/2008 | Palermo |
| 2009/0197202 A1 | | 8/2009 | Matsumura |
| 2009/0246343 A1 | | 10/2009 | Wu et al. |
| 2011/0070372 A1 | | 3/2011 | Faucher et al. |
| 2011/0070374 A1 | | 3/2011 | Ambrose et al. |
| 2011/0151128 A1 | | 6/2011 | Boggs et al. |
| 2011/0244157 A1 | | 10/2011 | Singer et al. |
| 2014/0011018 A1 | | 1/2014 | Diehl et al. |
| 2014/0023782 A1 | | 1/2014 | Kunz et al. |
| 2014/0030535 A1 | | 1/2014 | Makotky et al. |
| 2015/0225339 A1 | | 8/2015 | Niedermair et al. |
| 2015/0344732 A1 | | 12/2015 | Witt-Sanson et al. |
| 2016/0280951 A1 | | 9/2016 | Drumright et al. |

FOREIGN PATENT DOCUMENTS

| | | |
|---|---|---|
| CN | 102296290 A | 12/2011 |
| CN | 103145588 A | 6/2013 |
| CN | 103502354 A | 1/2014 |
| CN | 104955911 A | 9/2015 |
| EP | 0497526 A2 | 8/1992 |
| EP | 0519186 A1 | 12/1992 |
| EP | 0866082 A1 | 9/1998 |
| EP | 1525274 B1 | 4/2005 |
| EP | 1541640 A1 | 6/2005 |
| EP | 1935878 A1 | 6/2008 |
| EP | 2316868 A1 | 5/2011 |
| EP | 2447059 A2 | 5/2012 |
| EP | 2746353 A1 | 6/2014 |
| EP | 2773710 B1 | 4/2016 |
| JP | 63030070 B2 | 6/1988 |
| JP | H11335594 A | 12/1999 |
| JP | 2001192609 A | 7/2001 |
| JP | 5146327 B2 | 2/2013 |
| JP | 2014148618 A | 8/2014 |
| KR | 20100106505 A | 10/2010 |
| RU | 2376284 C1 | 10/2009 |
| RU | 2009103017 A | 8/2010 |
| WO | 2004000958 A1 | 12/2003 |
| WO | 2006132910 A1 | 12/2006 |
| WO | 2008076669 A1 | 6/2008 |
| WO | 2009095471 A1 | 8/2009 |
| WO | 2011019840 A1 | 2/2011 |
| WO | 2012118500 A1 | 9/2012 |
| WO | 2012118501 A1 | 9/2012 |
| WO | 2012162301 A1 | 11/2012 |
| WO | 2013191825 A1 | 12/2013 |
| WO | 2014025411 A1 | 2/2014 |
| WO | 2015077687 A1 | 5/2015 |

OTHER PUBLICATIONS

Machine English translation of CN 103145588.
Machine English translation of EP0519186.
Machine English translation of the Abstract only of JP2001192609.
Machine English translation of JPH11335594.
Machine English translation of RU2376284.

* cited by examiner

COATING COMPOSITION COMPRISING A THERMOSET RESIN AND A THERMOPLASTIC RESIN

The present invention relates to coating compositions. In particular, the present invention relates to coating compositions for coating onto a metal substrate, particularly onto a metal substrate for the packaging industry, such as coating onto food and/or beverage containers or aerosol cans. The invention also extends to metal substrates coated on at least of portion thereof with the thermoset powder coating composition.

The surfaces of such food and/or beverage container or aerosol cans are coated for various reasons. The external surfaces of such containers or cans are often coated in a decorative manner and may allow printing thereon to inform a user as to the contents of the container or can. The internal surfaces of such container or cans are typically coated to protect the container or can from the contents therein, which in some instances may be chemically aggressive. The coating on the container or can should also protect the contents from the container or can. There should be a minimal amount of alteration to the contents from materials that are products of erosion of the container or can, or from the coating itself. Accordingly, the coating composition used to coat the internal surfaces of the container or can should be designed such that it is able to withstand contact with these aggressive chemicals and to minimise the release of material from the metal of the container or can or the coating layer into the contents of the container or can.

A wide variety of coatings have been used to coat the above mentioned containers or cans. With regard to food and/or beverage containers, the coating compositions are required to have certain properties such as being capable of high speed application, having excellent adhesion to the substrate, being safe for food contact and having properties once cured that are suitable for their end use.

Cans used for the storage of aerosols, such as personal healthcare aerosols, are typically formed from a tube, for example, an aluminium tube. One such tube type is a monobloc aerosol, which is so called because it is formed from a single piece (a small disc known as a "slug") of aluminium. Coating compositions known in the art and used to coat such cans, particularly an internal portion thereof, include polyamide imide, which is made in N-methyl pyrrolidone. However, N-methyl pyrrolidone has recently been reclassified as toxic to reproduction and development (reprotoxic) and also listed as having specific organ toxicity for the respiratory tract and thus its use is not desirable.

Furthermore, many of the coating compositions currently used for food and/or beverage or aerosol applications contain epoxy resins. Such epoxy resins are typically formed from polyglycidyl ethers of bisphenol A (BPA). BPA is perceived as being harmful to human health and it is therefore desirable to eliminate it from coatings. Derivatives of BPA such as diglycidyl ethers of bisphenol A (BADGE), epoxy novolak resins and polyols prepared from BPA and bisphenol F (BPF) are also viewed as problematic.

According to a first aspect of the present invention there is provided a powder coating composition comprising:
 a) a thermoset resin comprising an acid functional polyester material,
 b) a thermoplastic resin and
 c) a crosslinker material, wherein the coating composition is substantially free of bisphenol A (BPA), bisphenol F (BPF), bisphenol A diglycidyl ether (BADGE) and bisphenol F diglycidyl ether (BFDGE).

"Powder" and like terms as used herein, refers to materials that are in the form of solid particulates, as opposed to materials which are in the liquid form.

The powder coating composition of the present invention is suitably a thermoset powder coating composition comprising a thermoset resin. Suitably, the thermoset resin comprises an acid functional polyester material (a). The acid functional polyester material suitably comprises the reaction product of a polyacid and a polyol.

"Polyacid" and like terms as used herein, refers to a compound having two or more carboxylic acid groups, such as two, three or four acid groups, and includes an ester of the polyacid (wherein one or more of the acid groups is esterified) or an anhydride. The polyacid is suitably an organic polyacid.

Suitably, the carboxylic acid groups of the polyacid may be connected by a bridging group selected from: an alkylene group; an alkenylene group; an alkynylene group; or an arylene group.

The acid functional polyester material may be formed from any suitable polyacid. Suitable examples include, but are not limited to one or more of the following: diacids such as, for example, maleic acid, fumaric acid, itaconic acid, adipic acid, azelaic acid, succinic acid, sebacic acid, glutaric acid, heptanoic acid, decanoic diacid, dodecanoic diacid, dodecanedioic acid, phthalic acid, isophthalic acid, 5-tert-butylisophthalic acid, tetrachlorophthalic acid, tetrahydrophthalic acid, naphthalene dicarboxylic acid, terephthalic acid, hexahydrophthalic acid, methyl hexahydrophthalic acid, dimethyl terephthalate, cyclohexane dicarboxylic acid, chlorendic anhydride, 1,3-cyclohexane dicarboxylic acid, 1,4-cyclohexane dicarboxylic acid, endomethylene tetrahydrophthalic acid and endoethylene hexahydrophthalic acid; triacids such as, for example, trimellitic acid; polyacids such as, for example, naphthalene tetracarboxylic acid, cyclohexanetetra carboxylic acid, cyclobutane tetracarboxylic and tricyclodecane polycarboxylic acid; esters and anhydrides of all the aforementioned acids and combinations thereof.

The polyacid may be selected from terephthalic acid; isophthalic acid; adipic acid; trimellitic anhydride; or combinations thereof.

The polyacid may comprise terephthalic acid and/or isophthalic acid. The polyacid may comprise at least 50 mol %, suitably at least 60 mol %, such as at least 70 mol %, or even at least 75 mol % of terephthalic acid and/or isophthalic acid based on the total number of moles of polyacid. The polyacid may comprise up to 100 mol %, suitably up to 95 mol %, such as up to 90 mol % of terephthalic acid and/or isophthalic acid based on the total number of moles of polyacid. The polyacid may comprise from 50 to 100 mol %, suitably from 60 to 100 mol %, such as from 70 to 100 mol %, or even from 75 to 100 mol % of terephthalic acid and/or isophthalic acid based on the total number of moles of polyacid. The polyacid may comprise from 50 to 95 mol %, suitably from 60 to 95 mol %, such as from 70 to 95 mol %, or even from 75 to 95 mol % of terephthalic acid and/or isophthalic acid based on the total number of moles of polyacid. The polyacid may comprise from 50 to 90 mol %, suitably from 60 to 90 mol %, such as from 70 to 90 mol %, or even from 75 to 90 mol % of terephthalic acid and/or isophthalic acid based on the total number of moles of polyacid. Suitably, the polyacid may comprise from 75 to 90 mol % of terephthalic acid and/or isophthalic acid based on the total number of moles of polyacid.

The polyacid may comprise a diacid. The diacid may comprise at least 60 mol %, suitably at least 70 mol %, such as at least 80 mol %, or even 85 mol % of terephthalic acid and/or isophthalic acid based on the total number of moles of diacid. The diacid may comprise up to 100 mol %, suitably up to 99.9 mol %, such as at least 99 mol %, or even up to 95 mol % of terephthalic acid and/or isophthalic acid based on the total number of moles of diacid. The polyacid may comprise from 60 to 100 mol %, suitably from 70 to 100 mol %, such as from 80 to 100 mol %, or even from 80 to 100 mol % of terephthalic acid and/or isophthalic acid based on the total number of moles of diacid. The polyacid may comprise from 60 to 99.9 mol %, suitably from 70 to 99.9 mol %, such as from 80 to 99.9 mol %, or even from 80 to 99.9 mol % of terephthalic acid and/or isophthalic acid based on the total number of moles of diacid. The polyacid may comprise from 60 to 99 mol %, suitably from 70 to 99 mol %, such as from 80 to 99 mol %, or even from 80 to 99 mol % of terephthalic acid and/or isophthalic acid based on the total number of moles of diacid. The polyacid may comprise from 60 to 95 mol %, suitably from 70 to 95 mol %, such as from 80 to 95 mol %, or even from 80 to 95 mol % of terephthalic acid and/or isophthalic acid based on the total number of moles of diacid. Suitably, the diacid may comprise from 75 to 100 mol % of terephthalic acid and/or isophthalic acid based on the total number of moles of diacid.

The acid functional polyester material may be formed from a polyacid comprising succinic acid, glutaric acid, adipic acid, heptanoic acid, dodecanedioic acid or combinations thereof. Suitably, the acid functional polyester material may be formed from a polyacid comprising succinic acid adipic acid, dodecanedioic acid or combinations thereof. It has surprisingly and advantageously been found by the present inventors that the presence of such polyacids in an acid functional polyester material results in a liquid coating composition, comprising such acid functional polyester materials, having a lower curing temperature than would typically be expected. It will be understood by a person skilled in the art that this is advantageous industrially and environmentally.

"Polyol" and like terms, as used herein, refers to a compound having two or more hydroxyl groups, such as two, three or four hydroxyl groups. The hydroxyl groups of the polyol may be connected by a bridging group selected from: an alkylene group; an alkenylene group; an alkynylene group; or an arylene group. Suitably the polyol is an organic polyol.

The acid functional polyester material may be formed from any suitable polyol. Suitable examples include, but are not limited to one or more of the following: diols such as, for example, alkylene glycols, such as ethylene glycol, diethylene glycol, dipropylene glycol, triethylene glycol, tripropylene glycol, hexylene glycol, polyethylene glycol, polypropylene glycol and neopentyl glycol; hydrogenated bisphenol A; cyclohexanediol; propanediols including 1,2-propanediol, 1,3-propanediol, butyl ethyl propanediol and 2-ethyl-2-butyl-1,3-propanediol; butanediols including 1,4-butanediol, 1,3-butanediol, butane-2,3-diol, 2-methyl-1,3-propanediol, tricyclodecane dimethanol-2,2,4,4-tetramethyl cyclobutane-1,3-diol and 2-ethyl-1,4-butanediol; pentanediols including trimethyl pentanediol and 2-methylpentanediol; cyclohexanedimethanol; hexanediols including 1,6-hexanediol, caprolactonediol (for example, the reaction product of epsilon-capro lactone and ethylene glycol); hydroxyalkylated bisphenols; polyether glycols, for example, poly(oxytetramethylene) glycol; dimethylol cyclohexane; triols such as, for example, trimethylol propane, trimethylol ethane, trimethylol butane and glycerol; polyols such as, for example, pentaerythritol and di-pentaerythritol; and the like or combinations thereof.

The polyester material may be formed from an unsaturated polyol. Suitable examples of unsaturated polyols include, but are not limited to one or more of the following: trimethylol propane monoallyl ether; trimethylol ethane monoallyl ether; prop-1-ene-1,3-diol or combinations thereof.

The polyol may be selected from neopentyl glycol; ethylene glycol; diethylene glycol; or combinations thereof.

The polyol may comprise neopentyl glycol. The polyol may comprise at least 10 mol %, suitably at least 20 mol %, such as at least 30 mol %, such as 40 mol %, or even at least 50 mol % of neopentyl glycol based on the total number of moles of polyol. The polyol may comprise up to 100 mol %, suitably up to 90 mol %, such as up to 80 mol %, or even up to 70 mol % of neopentyl glycol based on the total number of moles of polyol present. The polyol may comprise from 10 to 100 mol %, suitably from 10 to 90 mol %, such as from 10 to 80 mol %, or even from 10 to 70 mol % of neopentyl glycol based on the total number of moles of polyol present. The polyol may comprise from 20 to 100 mol %, suitably from 20 to 90 mol %, such as from 20 to 80 mol %, or even from 20 to 70 mol % of neopentyl glycol based on the total number of moles of polyol present. The polyol may comprise from 30 to 100 mol %, suitably from 30 to 90 mol %, such as from 30 to 80 mol %, or even from 30 to 70 mol % of neopentyl glycol based on the total number of moles of polyol present. The polyol may comprise from 40 to 100 mol %, suitably from 40 to 90 mol %, such as from 40 to 80 mol %, or even from 40 to 70 mol % of neopentyl glycol based on the total number of moles of polyol present. The polyol may comprise from 50 to 100 mol %, suitably from 50 to 90 mol %, such as from 50 to 80 mol %, or even from 50 to 70 mol % of neopentyl glycol based on the total number of moles of polyol present. Suitably, the polyol may comprise from 50 to 70 mol % of neopentyl glycol based on the total number of moles of polyol present.

The polyol may comprise a diol. The diol may comprise at least 10 mol %, suitably at least 20 mol %, such as at least 30 mol %, such as 40 mol %, or even at least 50 mol % of neopentyl glycol based on the total number of moles of diol. The diol may comprise up to 100 mol %, suitably up to 90 mol %, such as up to 80 mol %, or even up to 70 mol % of neopentyl glycol based on the total number of moles of diol present. The diol may comprise from 10 to 100 mol %, suitably from 10 to 90 mol %, such as from 10 to 80 mol %, or even from 10 to 70 mol % of neopentyl glycol based on the total number of moles of diol present. The diol may comprise from 20 to 100 mol %, suitably from 20 to 90 mol %, such as from 20 to 80 mol %, or even from 20 to 70 mol % of neopentyl glycol based on the total number of moles of diol present. The diol may comprise from 30 to 100 mol %, suitably from 30 to 90 mol %, such as from 30 to 80 mol %, or even from 30 to 70 mol % of neopentyl glycol based on the total number of moles of diol present. The diol may comprise from 40 to 100 mol %, suitably from 40 to 90 mol %, such as from 40 to 80 mol %, or even from 40 to 70 mol % of neopentyl glycol based on the total number of moles of diol present. The diol may comprise from 50 to 100 mol %, suitably from 50 to 90 mol %, such as from 50 to 80 mol %, or even from 50 to 70 mol % of neopentyl glycol based on the total number of moles of diol present. Suitably, the diol may comprise from 50 to 70 mol % of neopentyl glycol based on the total number of moles of diol present.

The term "alk" or "alkyl", as used herein unless otherwise defined, relates to saturated hydrocarbon radicals being straight, branched, cyclic or polycyclic moieties or combinations thereof and contain 1 to 20 carbon atoms, suitably 1 to 10 carbon atoms, more suitably 1 to 8 carbon atoms, still more suitably 1 to 6 carbon atoms, yet more suitably 1 to 4 carbon atoms.

These radicals may be optionally substituted with a chloro, bromo, iodo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{27}$, $C(O)SR^{27}$, $C(S)NR^{25}R^{26}$, aryl or Het, wherein $R^{19}$ to $R^{27}$ each independently represent hydrogen, aryl or alkyl, and/or be interrupted by one or more oxygen or sulphur atoms, or by silano or dialkylsiloxane groups. Examples of such radicals may be independently selected from methyl, ethyl, n-propyl, isopropyl, n-butyl, isobutyl, sec-butyl, tert-butyl, 2-methylbutyl, pentyl, iso-amyl, hexyl, cyclohexyl, 3-methylpentyl, octyl and the like. The term "alkylene", as used herein, relates to a bivalent radical alkyl group as defined above. For example, an alkyl group such as methyl which would be represented as —$CH_3$, becomes methylene, —$CH_2$—, when represented as an alkylene. Other alkylene groups should be understood accordingly.

The term "alkenyl", as used herein, relates to hydrocarbon radicals having one or several, suitably up to 4, double bonds, being straight, branched, cyclic or polycyclic moieties or combinations thereof and containing from 2 to 18 carbon atoms, suitably 2 to 10 carbon atoms, more suitably from 2 to 8 carbon atoms, still more suitably 2 to 6 carbon atoms, yet more suitably 2 to 4 carbon atoms. These radicals may be optionally substituted with a hydroxyl, chloro, bromo, iodo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{27}$, $C(O)SR^{27}$, $C(S)NR^{25}R^{26}$, or aryl, wherein $R^{19}$ to $R^{27}$ each independently represent hydrogen, aryl or alkyl, and/or be interrupted by one or more oxygen or sulphur atoms, or by silano or dialkylsiloxane groups. Examples of such radicals may be independently selected from alkenyl groups include vinyl, allyl, isopropenyl, pentenyl, hexenyl, heptenyl, cyclopropenyl, cyclobutenyl, cyclopentenyl, cyclohexenyl, 1-propenyl, 2-butenyl, 2-methyl-2-butenyl, isoprenyl, farnesyl, geranyl, geranylgeranyl and the like. The term "alkenylene", as used herein, relates to a bivalent radical alkenyl group as defined above. For example, an alkenyl group such as ethenyl which would be represented as —CH=CH2, becomes ethenylene, —CH=CH—, when represented as an alkenylene. Other alkenylene groups should be understood accordingly.

The term "alkynyl", as used herein, relates to hydrocarbon radicals having one or several, suitably up to 4, triple bonds, being straight, branched, cyclic or polycyclic moieties or combinations thereof and having from 2 to 18 carbon atoms, suitably 2 to 10 carbon atoms, more suitably from 2 to 8 carbon atoms, still more suitably from 2 to 6 carbon atoms, yet more suitably 2 to 4 carbon atoms. These radicals may be optionally substituted with a hydroxy, chloro, bromo, iodo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{27}$, $C(O)SR^{27}$, $C(S)NR^{25}R^{26}$, or aryl, wherein $R^{19}$ to $R^{27}$ each independently represent hydrogen, aryl or lower alkyl, and/or be interrupted by one or more oxygen or sulphur atoms, or by silano or dialkylsiloxane groups. Examples of such radicals may be independently selected from alkynyl radicals include ethynyl, propynyl, propargyl, butynyl, pentynyl, hexynyl and the like. The term "alkynylene", as used herein, relates to a bivalent radical alkynyl group as defined above. For example, an alkynyl group such as ethynyl which would be represented as —C≡CH, becomes ethynylene, —C≡C—, when represented as an alkynylene. Other alkynylene groups should be understood accordingly.

The term "aryl" as used herein, relates to an organic radical derived from an aromatic hydrocarbon by removal of one hydrogen, and includes any monocyclic, bicyclic or polycyclic carbon ring of up to 7 members in each ring, wherein at least one ring is aromatic. These radicals may be optionally substituted with a hydroxy, chloro, bromo, iodo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{27}$, $C(O)SR^{27}$, $C(S)NR^{25}R^{26}$, or aryl, wherein $R^{19}$ to $R^{27}$ each independently represent hydrogen, aryl or lower alkyl, and/or be interrupted by one or more oxygen or sulphur atoms, or by silano or dialkylsilcon groups. Examples of such radicals may be independently selected from phenyl, p-tolyl, 4-methoxyphenyl, 4-(tert-butoxy)phenyl, 3-methyl-4-methoxyphenyl, 4-fluorophenyl, 4-chlorophenyl, 3-nitrophenyl, 3-aminophenyl, 3-acetamidophenyl, 4-acetamidophenyl, 2-methyl-3-acetamidophenyl, 2-methyl-3-aminophenyl, 3-methyl-4-aminophenyl, 2-amino-3-methylphenyl, 2,4-dimethyl-3-aminophenyl, 4-hydroxyphenyl, 3-methyl-4-hydroxyphenyl, 1-naphthyl, 2-naphthyl, 3-amino-1-naphthyl, 2-methyl-3-amino-1-naphthyl, 6-amino-2-naphthyl, 4,6-dimethoxy-2-naphthyl, tetrahydronaphthyl, indanyl, biphenyl, phenanthryl, anthryl or acenaphthyl and the like. The term "arylene", as used herein, relates to a bivalent radical aryl group as defined above. For example, an aryl group such as phenyl which would be represented as —Ph, becomes phenylene, —Ph—, when represented as an arylene. Other arylene groups should be understood accordingly.

For the avoidance of doubt, the reference to alkyl, alkenyl, alkynyl, aryl or aralkyl in composite groups herein should be interpreted accordingly, for example the reference to alkyl in aminoalkyl or alk in alkoxyl should be interpreted as alk or alkyl above etc.

As used herein, unless otherwise expressly specified, all numbers such as those expressing values, ranges, amounts or percentages may be read as if prefaced by the word "about", even if the term does not expressly appear. Also, any numerical range recited herein is intended to include all sub-ranges subsumed therein. Singular encompasses plural and vice versa. For example, although reference is made herein to, for example, "a" thermoset resin, "a" thermoplastic resin, "a" crosslinker, "an" alkanol amine, "the" residue of "an", and the like, one or more of each of these and any other components can be used. As used herein, the term "polymer" refers to oligomers and both homopolymers and copolymers, and the prefix "poly" refers to two or more. Including, for example and like terms means including for example but not limited to. When ranges are given, any endpoints of those ranges and/or numbers within those ranges can be.

The acid functional polyester material may be formed from any suitable molar ratio of polyacid to polyol. The molar ratio of polyacid to polyol in the polyester material may be from 20:1 to 1:20, suitably from 10:1 to 1:10, such as from 5:1 to 1:5, or even from 2:1 to 1:2. Suitably, the molar ratio of polyacid to polyol in the polyester material may be 1:1.

The acid functional polyester material may comprise a polyol comprising a diacid and a triacid and a diol. It will be appreciated by a person skilled in the art that the amount of triacid present will influence the acid number of the acid functional polyester material.

The acid functional polyester material may optionally be formed from one or more additional monomers. Suitably, the acid functional polyester material may optionally include one or more additional monomers selected from monoacids or monohydric alcohols or combinations thereof. Suitably, the optional additional monomers may be organic.

The acid functional polyester material may optionally be formed from an additional monoacid. "Monoacid", and like terms as used herein, refers to compounds having one carboxylic acid group and includes an ester of the monoacid (where the acid group is esterified) or an anhydride. The monoacid is suitably an organic monoacid.

The acid functional polyester material may optionally be formed from any suitable additional monoacid. Suitable examples include, but are not limited to one or more of the following: benzoic acid; cyclohexane carboxylic acid; tri-cyclodecane carboxylic acid; camporic acid; benzoic acid; t-butyl benzoic acid; $C_1$-$C_{18}$ aliphatic carboxylic acids such as acetic acid; propanoic acid; butanoic acid; hexanoic acid; oleic acid; linoleic acid; undecanoic acid; lauric acid; isononanoic acid; fatty acids; hydrogenated fatty acids of naturally occurring oils; esters and/or anhydrides of any of the aforementioned acids and combinations thereof.

The acid functional polyester material may optionally be formed from an additional monohydric alcohol. "Monohydric alcohol" and like terms as used herein, refers to compounds having one hydroxyl group. Suitably, the monohydric alcohol is an organic monohydric alcohol.

The acid functional polyester material may optionally be formed from any suitable additional monohydric alcohol. Suitable examples include but are not limited to one or more of the following: benzyl alcohol; hydroxyethoxybenzene; methanol; ethanol; propanol; butanol; pentanol; hexanol; heptanol; dodecyl alcohol; stearyl alcohol; oleyl alcohol; undecanol;

cyclohexanol; phenol; phenyl carbinol; methylphenyl carbinol; cresol; monoethers of glycols; halogen-substituted or other substituted alcohols and combinations thereof.

The acid functional polyester material may have an acid number (AN) of at least 25 mg KOH/g. Suitably, the polyester material may have an acid number from 25 to 100 mg KOH/g, such as from 30 to 100 mg KOH/g or even from 50 to 90 mg KOH/g. The acid functional polyester material may have an acid number from 50 to 80 mg KOH/g.

The acid functional polyester material may have an acid number from 65 to 75 mg KOH/g.

The acid functional polyester material may have an acid number from 30 to 40 mg KOH/g.

Suitably, the acid number (AN) is expressed on solids.

The acid number (AN) of the acid functional polyester material may be measured by any suitable method. Methods to measure AN will be well known to a person skilled in the art. In such a method, suitably, the AN is determined by titration with 0.1M methanolic potassium hydroxide (KOH) solution. A sample of solid polyester (typically, 0.1 to 3g) is weighed accurately into a conical flask and is dissolved, using light heating and stirring as appropriate, in 25 ml of dimethyl formamide containing phenolphthalein indicator. The solution is then cooled to room temperature and titrated with the 0.1M methanolic potassium hydroxide solution. The resulting acid number is expressed in units of mg KOH/g and is calculated using the following equation:

$$\text{Acid number} = \frac{\text{titre of KOH solution (ml)} \times \text{molarity KOH solution (M)} \times 56.1}{\text{weight of solid sample (g)}}$$

All values for acid number (AN) reported herein were measured this way.

The acid functional polyester material may have any suitable gross hydroxyl value (OHV). The acid functional polyester material may have a gross OHV up to 5.0 mg KOH/g. Suitably, the acid functional polyester material may have a gross OHV from 0 to 5.0 mg KOH/g, such as from 0 to 0.4 KOH/g or even from 0 to 3.0 KOH/g.

Suitably, the gross hydroxyl value (OHV) is expressed on solids.

The gross hydroxyl value (OHV) of the acid functional polyester material may be measured by any suitable method. Methods to measure OHV will be well known to a person skilled in the art. Suitably, the hydroxyl value is the number of mg of KOH equivalent to the hydroxyl groups in 1 g of material. In such as method, suitably, a sample of solid polyester (typically, 0.1 to 3g) is weighed accurately into a conical flask and is dissolved, using light heating and stirring as appropriate, in 20 ml of tetrahydrofuran. 10 ml of 0.1M 4-(dimethylamino)pyridine in tetrahydrofuran (catalyst solution) and 5 ml of a 9 vol % solution of acetic anhydride in tetrahydrofuran (i.e. 90 ml acetic anhydride in 910 ml tetrahydrofuran; acetylating solution) are then added to the mixture. After 5 minutes, 10 ml of an 80 vol % solution of tetrahydrofuran (i.e. 4 volume parts tetrahydrofuran to 1 part distilled water; hydrolysis solution) us added. After 15 minutes, 10 ml tetrahydrofuran is added and the solution is titrated with 0.5M ethanolic potassium hydroxide (KOH). A blank sample is also run where the sample of solid polyester is omitted. The resulting hydroxyl number is expressed in units of mg KOH/g and is calculated using the following equation:

$$\text{Hydroxyl value} = \frac{(V_2 - V_1) \times \text{molarity of KOH solution (M)} \times 56.1}{\text{weight of solid sample (g)}}$$

wherein $V_1$ is the titre of KOH solution (ml) of the polyester sample and $V_2$ is the titre of KOH solution (ml) of the blank sample.

All values for gross hydroxyl value (OHV) reported herein were measured this way.

The acid functional polyester material may have any suitable glass transition temperature (Tg). The acid functional polyester material may have a Tg of at least 20° C., suitably at least 30° C., such as at least 40° C., or even at least 50° C. The acid functional polyester material may have a Tg of up to 150° C., suitably up to 120° C., such as up to 100° C., or even up to 80° C. The acid functional polyester material may have a Tg from 20° C. to 150° C., suitably from 20° C. to 120° C., such as from 20° C. to 100° C., or even from 20° C. to 80° C. The acid functional polyester material may have a Tg from 30° C. to 150° C., suitably from 30° C. to 120° C., such as from 30° C. to 100° C., or even from 30° C. to 80° C. The acid functional polyester material may have a Tg from 40° C. to 150° C., suitably from 40° C. to 120° C., such as from 40° C. to 100° C., or even from 40° C. to 80° C. The acid functional polyester material may have a Tg from 50° C. to 150° C., suitably from 50° C. to 120° C., such as from 50° C. to 100° C., or even from 50° C. to 80° C.

Suitably, the acid functional polyester material may have a Tg from 60° C. to 70° C.

The Tg of the acid functional polyester material may be measured by any suitable method. Methods to measure Tg will be well known to a person skilled in the art. Suitably, the Tg is measured according to ASTM D6604-00(2013) ("Standard Practice for Glass Transition Temperatures of Hydrocarbon Resins by Differential Scanning calorimetry". Heat-flux differential scanning calorimetry (DSC), sample pans: aluminium, reference: blank, calibration: indium and mercury, sample weight: 10mg, heating rate: 20° C./min). All values for glass transition temperature (Tg) reported herein were measured this way.

The acid functional polyester material according to the first aspect of the present invention may have any suitable melt viscosity at 200° C. The acid functional polyester material may have a melt viscosity at 200° C. from 2 to 100 Poise, suitably from 5 to 70 Poise, such as from 10 to 50 Poise, or even from 20 to 40 Poise. The acid functional polyester material may have a melt viscosity at 200° C. of at least 2 Poise, suitably at least 5 Poise, such as at least 10 Poise, or even at least 20 Poise. The acid functional polyester material may have a melt viscosity at 200° C. of up to 100 Poise, suitably up to 70 Poise, such as up to 50 Poise, or even up to 40 Poise. The acid functional polyester material may have a melt viscosity at 200° C. from 2 to 100 Poise, suitably from 2 to 70 Poise, such as from 2 to 50 Poise, or even from 2 to 40 Poise. The acid functional polyester material may have a melt viscosity at 200° C. from 5 to 100 Poise, suitably from 5 to 70 Poise, such as from 5 to 50 Poise, or even from 5 to 40 Poise. The acid functional polyester material may have a melt viscosity at 200° C. from 10 to 100 Poise, suitably from 10 to 70 Poise, such as from 10 to 50 Poise, or even from 10 to 40 Poise. The acid functional polyester material may have a melt viscosity at 200° C. from 20 to 100 Poise, suitably from 20 to 70 Poise, such as from 20 to 50 Poise, or even from 20 to 40 Poise.

The melt viscosity of the acid functional polyester material may be measured by any suitable method. Methods to measure melt viscosity will be well known to a person skilled in the art. Suitably, melt viscosity is determined using a cone and plate viscometer with a heated plate with cones which can be selected together with appropriate rotational speeds to measure viscosities within the desired ranges. Suitably, a Brookfield CAP 2000+ machine which is capable of measuring viscosities at temperatures of 100 to 250° C. is used. The temperature selected for the measurement is held constant throughout the measurement time and the detail of the temperature used is suitably recorded for each measurement. Suitably, the cone used is a spindle no. 6 and the speed of rotation is selected so as to ensure that the range of measurements falls well within the total measurement range. All values for melt viscosity reported herein were measured this way.

The acid functional polyester material of the present invention may have any suitable number-average molecular weight (Mn). The acid functional polyester material may have an Mn from 500 Daltons (Da=g/mole), suitably from 1,000 Da, such as from 2,000 Da or even from 5,000 Da. The acid functional polyester material may have an Mn up to 200,000 Da, suitably up to 100,000 Da, such as up to 50,000 Da or even up to 20,000 Da.

The acid functional polyester material may have an Mn from 500 to 200,000 Da, suitably from 1,000 to 200,000 Da, such as from 2,000 to 200,000 Da or even from 5,000 to 200,000 Da. The acid functional polyester material may have an Mn from 500 to 100,000 Da, suitably from 1,000 to 100,000 Da, such as from 2,000 to 100,000 Da or even from 5,000 to 100,000 Da. The acid functional polyester material may have an Mn from 500 to 50,000 Da, suitably from 1,000 to 50,000 Da, such as from 2,000 to 50,000 Da or even from 5,000 to 50,000 Da. The acid functional polyester material may have an Mn from 500 to 20,000 Da, suitably from 1,000 to 20,000 Da, such as from 2,000 to 20,000 Da or even from 5,000 to 20,000 Da.

The number-average molecular weight (Mn) may be measured by any suitable method. Techniques to measure the number-average molecular weight will be well known to a person skilled in the art. Suitably, the Mn may be determined by gel permeation chromatography using a polystyrene standard according to ASTM D6579-11("Standard Practice for Molecular Weight Averages and Molecular Weight Distribution of Hydrocarbon, Rosin and Terpene Resins by Size Exclusion Chromatography". UV detector; 254 nm, solvent: unstabilised THF, retention time marker: toluene, sample concentration: 2 mg/ml). All values for number-average molecular weight (Mn) reported herein were measured this way.

The acid functional polyester material of the present invention may have any suitable weight-average molecular weight (Mw). The acid functional polyester material may have an Mw from 500 Daltons (Da =g/mole), suitably from 1,000 Da, such as from 2,000 Da or even from 5,000 Da. The acid functional polyester material may have an Mw up to 200,000 Da, suitably up to 100,000 Da, such as up to 50,000 Da or even up to 20,000 Da.

The acid functional polyester material may have an Mw from 500 to 200,000 Da, suitably from 1,000 to 200,000 Da, such as from 2,000 to 200,000 Da or even from 5,000 to 200,000 Da. The acid functional polyester material may have an Mw from 500 to 100,000 Da, suitably from 1,000 to 100,000 Da, such as from 2,000 to 100,000 Da or even from 5,000 to 100,000 Da. The acid functional polyester material may have an Mw from 500 to 50,000 Da, suitably from 1,000 to 50,000 Da, such as from 2,000 to 50,000 Da or even from 5,000 to 50,000 Da. The acid functional polyester material may have an Mw from 500 to 20,000 Da, suitably from 1,000 to 20,000 Da, such as from 2,000 to 20,000 Da or even from 5,000 to 20,000 Da.

A person skilled in the art will appreciate that techniques to measure the number-average molecular weight may also be applied to measure the weight-average molecular weight. All values for weight-average molecular weight (Mw) reported herein were measured this way.

The acid functional polyester material according to any aspect of the present invention may be in solid form at room temperature and at atmospheric pressure.

The acid functional polyester material of the present invention may have a glass transition temperature (Tg) from 50 to 100° C. and a viscosity from 10 to 50 Poise at 200° C.

The coating compositions of the present invention comprise a thermoplastic resin (b). The coating compositions may comprise any suitable thermoplastic resin. Suitable examples of thermoplastic resins include, but are not limited to, one or more of the following: epoxy resins; polyester resins; polyolefin resins; polyurethane resins; polysiloxane resins; acrylic resins; hydrocarbon resins; polyamide or combinations thereof. Suitably, the thermoplastic resin may comprise polyolefin resins, acrylic resins or a combination thereof.

The thermoplastic resin may comprise a polyolefin resin.
The thermoplastic resin may comprise an acrylic resin.
The thermoplastic resin may comprise a polyolefin resin and an acrylic resin.

The thermoplastic resin of the present invention may have any suitable glass transition temperature (Tg). The thermoplastic resin may have a Tg of at least 20° C., suitably at least 25 ° C., such as at least 30° C., or even at least 40° C. The thermoplastic resin may have a Tg of up to 150° C., suitably up to 120° C., such as up to 100° C., or even up to 80° C. The thermoplastic resin may have a Tg from 20° C. to 150° C., suitably from 20° C. to 120° C., such as from 20° C. to 100° C., or even from 20° C. to 80° C. The thermoplastic resin may have a Tg from 25° C. to 150 ° C., suitably from 25° C. to 120° C., such as from 25° C. to 100° C., or even from 25° C. to 80° C. The thermoplastic resin may have a Tg from 30° C. to 150° C., suitably from 30° C. to 120° C., such as from 30° C. to 100° C., or even from 30° C. to 80° C. The thermoplastic resin may have a Tg from 40° C. to 150° C., suitably from 40° C. to 120° C., such as from 40° C. to 100° C., or even from 40° C. to 80° C.

Suitably, the thermoplastic resin may have a Tg from 40 to 80° C.

The thermoplastic resin may have a Tg from 40 to 70° C.

The Tg of the thermoplastic resin may be measured by any suitable method. Methods to measure Tg will be well known to a person skilled in the art. Suitably, the Tg is measured according to ASTM D6604-00(2013) ("Standard Practice for Glass Transition Temperatures of Hydrocarbon Resins by Differential Scanning calorimetry". Heat-flux differential scanning calorimetry (DSC), sample pans: aluminium, reference: blank, calibration: indium and mercury, sample weight: 10 mg, heating rate: 20° C./min). All glass transition temperatures (Tg) reported herein were measured this way.

The thermoplastic resin of the present invention may have any suitable number-average molecular weight (Mn).

The number-average molecular weight may be measured by any suitable method. Techniques to measure the number-average molecular weight will be well known to a person skilled in the art. Suitably, the Mn may be determined by gel permeation chromatography using a polystyrene standard according to ASTM D6579-11 ("Standard Practice for Molecular Weight Averages and Molecular Weight Distribution of Hydrocarbon, Rosin and Terpene Resins by Size Exclusion Chromatography". UV detector; 254 nm, solvent: unstabilised THF, retention time marker: toluene, sample concentration: 2 mg/ml). All values for number-average molecular weight (Mn) reported herein were measured this way.

The thermoplastic resin of the present invention may have any suitable weight-average molecular weight (Mw).

A person skilled in the art will appreciate that techniques to measure the number-average molecular weight may also be applied to measure the weight-average molecular weight. All values for weight-average molecular weight (Mw) reported herein were measured this way.

The thermoplastic resin of the present invention suitably has a melt index (MI) between 2 and 50 g per 10 min. Where the thermoplastic resin comprises polyamide, the polyamide suitable has a melt index of between 27 and 50 g per 10 min.

The melt index is measured according to ISO 1133-1:2011 method B (displacement-measurement method) at a temperature of 230° C. and a nominal load of 2.66 kg. All values for melt index reported herein were measured this way.

A person skilled in the art will appreciate that techniques to measure the melt viscosity of the acid functional polyester material may also be applied to measure the melt viscosity of the thermoplastic resin. All values for melt index reported herein were measured this way.

The thermoset powder coating composition of the present invention may comprise a commercially available thermoplastic resin such as, nylon resins or for example, those available under the trade name Surlyn (available from DuPont).

The thermoplastic resin may be provided in the form of a granular solid or in the form of a dispersion in a liquid carrier.

When the thermoplastic resin is provided in the form of a granular solid, the granular solid may be formed by any suitable method. The granular solid thermoplastic resin, may be extruded in combination with the thermoset material. Suitable methods will be well known to a person skilled in the art. Suitably, the extruded thermoset and thermoplastic resin is ground to a powder.

The thermoplastic resin may comprise a polyolefin resin granular solid.

The thermoplastic resin may comprise an acrylic resin granular solid.

The thermoplastic resin may comprise a polyolefin resin granular solid and an acrylic resin granular solid.

For the avoidance of doubt, a dispersion as described herein is a granular solid phase, such as a powder, suspended in a liquid carrier. The liquid carrier, when present, may comprise water, an organic solvent, a mixture of water and one or more organic solvent(s) or a mixture of organic solvents. Suitably, the liquid carrier may comprise water.

It has surprisingly and advantageously been found by the present inventors that the acid functional polyester materials of the present invention are hydrolytically stable.

Suitable organic solvents include, but are not limited to one or more of the following: aliphatic hydrocarbons such as mineral spirits and high flash point naphtha; aromatic hydrocarbons such as benzene; toluene; xylene; solvent naphtha 100, 150, 200; those available from Exxon-Mobil Chemical Company under the SOLVESSO trade name; alcohols such as ethanol; n-propanol; isopropanol; and n-butanol; ketones such as acetone; cyclohexanone; methylisobutyl ketone;

methyl ethyl ketone; esters such as ethyl acetate; butyl acetate; n-hexyl acetate; glycols such as butyl glycol; glycol ethers such as methoxypropanol; ethylene glycol monomethyl ether; ethylene glycol monobutyl ether and combinations thereof.

The thermoplastic resin may comprise a polyolefin resin, an acrylic resin or a combination thereof dispersed in a liquid carrier. Suitably, the thermoplastic resin may comprise a polyolefin resin, an acrylic resin or a combination thereof dispersed in water.

The thermoplastic resin may comprise a polyolefin resin dispersed in a liquid carrier, suitably dispersed in water.

The thermoplastic resin may comprise an acrylic resin dispersed in a liquid carrier, suitably dispersed in water.

The thermoplastic resin may comprise a polyolefin resin and an acrylic resin dispersed in a liquid carrier, suitably dispersed in water.

It will be appreciated by a person skilled in the art that when the thermoplastic resin is provided in the form of a dispersion, the liquid carrier must be removed in order to form the powder coating compositions of the present invention. When the thermoplastic resin is provided in the form of a dispersion, the liquid carrier may be removed prior to the formation of the powder coating composition or during the formation of the powder coating composition. Suitably, the liquid carrier may be removed prior to the formation of the powder coating composition.

The powder coating composition of the present invention comprises a crosslinker material. The crosslinker material may comprise any suitable crosslinker material. Suitable crosslinker materials will be well known to the person skilled in the art. Suitable crosslinker materials include, but are not limited to, one or more of the following: phenolic resins (or phenol-formaldehyde resins); aminoplast resins (or triazine-formaldehyde resins); amino resins; epoxy resins; epoxy-mimic resins, such as those based on bisphenols and other bisphenol A (BPA) replacements; isocyanate resins, isocyanurate resins, such as triglycidylisocyanurate; hydroxy (alkyl) amide resins, such as β-hydroxy (alkyl) amide resins; hydroxy(alkyl) urea resins; carbodiimide resins; oxazolines; polyamines; polyamides and combinations thereof.

The crosslinker material may be selected from hydroxy (alkyl) amide resins, such as β-hydroxy (alkyl) amide resins; hydroxy(alkyl) urea resins; carbodiimide resins; oxazolines; isocyanurate resins, such as triglycidylisocyanurate; epoxy-mimic resins, such as those based on bisphenols and other bisphenol A (BPA) replacements; or combinations thereof. Suitably, the crosslinker material may be selected from hydroxy (alkyl) amide resins, such as β-hydroxy (alkyl) amide resins; hydroxy(alkyl) urea resins; or combinations thereof.

Suitably, the crosslinker material comprises a hydroxyalkylamide material and/or a hydroxyalkylurea material and/or a carbodiimide resin. Suitably, the crosslinker material comprises a hydroxyalkylamide material and/or a hydroxyalkylurea material.

Suitably, the crosslinker material may be operable to crosslink the acid functionality on the acid functional polyester material.

The crosslinker material may contain nitrogen. The crosslinker material may be in the form of an amine or amide material. The crosslinker material may comprise a hydroxyl substituted amine or amide material.

Suitably, the crosslinker material may comprise a hydroxyalkylamide material, such as a β-hydroxyalkylamide material.

The crosslinker material may contain a terminal chemical group as shown in Formula I.

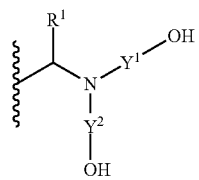

Formula I wherein $R^1$ represents an electron withdrawing group, such as (=O); and $Y^1$ and $Y^2$ each, independently, represents a $C_1$ to $C_3$ alkylene group.

The terminal chemical group of Formula I may be connected to a further chemical structure, not shown. Additionally or alternatively, the chemical group of formula I may be suspended from a carrier substrate, such as a silica carrier substrate, for example.

The hydroxyalkylamide crosslinker may contain a plurality of terminal chemical groups as shown in Formula I. For example, the hydroxyalkylamide crosslinker may contain 2, 3 or 4 terminal chemical groups as shown in Formula I.

The hydroxyalkylamide crosslinker may comprise a moiety according to Formula II:

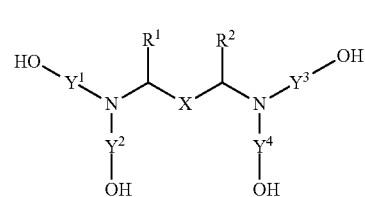

Formula II wherein $R^1$ and $R^2$ with reference to Formula II each, independently, represent an electron withdrawing group, such as (=O); $Y^1$, $Y^2$, $Y^3$ and $Y^4$ with reference to Formula II each, independently, represent a $C_1$ to $C_3$ alkylene group; and X is a $C_2$ to $C_6$ alkylene group.

Suitably, each of $R^1$ and $R^2$ with reference to Formula II represents a (=O) group.

Suitably, each of Y1, Y2, Y3 and Y4 with reference to Formula II represent an ethylene group.

Suitably, X represents a butylene group.

Accordingly, the hydroxyalkylamide crosslinker comprises a material of formula III:

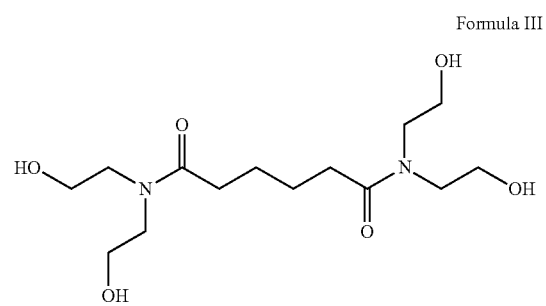 [SMILES: O=C(CCCCC(=O)N(CCO)CCO)N(CCO)CCO]

Formula III

The coating composition of the present invention may comprise a commercially available hydroxyalkylamide crosslinker such as, for example, PRIMID XL-552 (available from EMS Chemie); PRIMID QM-1260 (available from EMS Chemie); PRIMID SF-4510 (available from EMS Chemie) and N,N,N',N'-tetrakis(2-hydroxypropyl)adipamide.

The crosslinker may be in the form of a urea material. The crosslinker may comprise a hydroxyl substituted urea material.

Suitably, the crosslinker may comprise a hydroxy functional alkyl polyurea material.

The crosslinker may contain a terminal chemical group as shown in Formula IV.

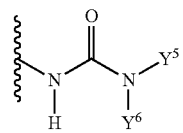

Formula IV wherein $Y^5$ and $Y^6$ each, independently, represent hydrogen, an alkyl or a hydroxy functional alkyl having two or more carbon atoms and at least one of $Y^5$ and $Y^6$ is a hydroxyl functional alkyl having two or more carbon atoms.

The $Y^5$ and $Y^6$ groups may exclude ether linkages.

The terminal chemical group of Formula IV may be connected to a further chemical structure, not shown. Additionally or alternatively, the chemical group of Formula IV may be suspended from a carrier substrate, such as a silica carrier substrate, for example.

The crosslinker may contain a plurality of terminal chemical groups as shown in Formula IV. For example, the crosslinker may contain 2 to 6 terminal chemical groups as shown in Formula IV, such as 2, 3 or 4 terminal chemical groups as shown in Formula IV.

The crosslinker material may comprise a moiety according to Formula V:

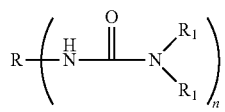

Formula V wherein R with reference to Formula V comprises the residue of an isocyanurate, biuret, allophonate, glycoluril, benzoguanamine, polyetheramine, and/or polymeric moiety having an Mn of 500 or greater; each $R_1$ with reference to Formula V is independently a hydrogen, an alkyl or a hydroxy functional alkyl having 2 or more carbons and at least one $R_1$ with reference to Formula V is a hydroxy functional alkyl having 2 or more carbons; and n is 2-6.

Suitably, the $R_1$ group with reference to Formula V may exclude ether linkages.

20

The crosslinker may comprise a moiety according to Formula VI:

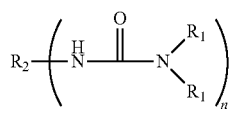

Formula VI wherein $R_2$ with reference to Formula VI comprises a substituted or unsubstituted $C_1$ to $C_{36}$ alkyl group, an aromatic group, or the residue of an isocyanurate, biuret, allophonate, glycoluril, benzoguanamine, polyetheramine, and/or a polymeric moiety having an Mn of 500 or greater; each $R_1$ with reference to Formula VI is independently a hydrogen, an alkyl group having 1 or more carbons, or a hydroxy functional alkyl having 2 or more carbons and at least one $R_1$ with reference to Formula VI is a hydroxy functional alkyl having 2 or more carbons; and n is 2-6.

Suitably, when $R_2$ with reference to Formula VI is a substituted or unsubstituted $C_1$ to $C_{36}$ alkyl group the acid functional polyester material comprises COOH functionality that reacts with the polyurea to form an ester linkage.

Suitably, the $R_1$ group with reference to Formula VI may exclude ether linkages.

It will be understood that when $R_2$ with reference to Formula VI is a substituted or unsubstituted alkyl group, there may be two $R_2$ groups with reference to Formula VI attached to the N, and the two $R_2$ groups with reference to Formula VI may be the same or different. For example, if the hydroxy functional alkyl polyurea is formed from the reaction of dimethyl carbonate with dibutylamine and diisopropanol amine, there will be two $R_2$ groups with reference to Formula VI that will each be C4.

R and $R_2$ with reference to Formula VI may comprise the residue of an isocyanurate, biuret, allophonate, glycoluril, benzoguanamine, polyetheramine and/or polymeric moiety having an Mn of 500 or greater. An isocyanurate will be understood as referring to a compound having three isocyanate groups, typically in ring form, and is sometimes referred to as a trimer. This can include compounds having one or more isocyanurate moieties. Isocyanurates can be purchased from Covestro and Vencore X Chemical. Suitable commercially available isocyanurates include those sold under the trade name DESMODUR such as, for example, DESMODUR N 3300A, DESMODUR N3800, DESMODUR N3790, DESMODUR N3400, DESMODUR N3600, DESMODUR N3900 and DESMODUR RC (commercially available from Covestro), those sold under the trade name VESTANANT such as, for example, VESTANAT T1890/100 (commercially available from Evonik) and those sold under the trade name EASAQUA such as, for example, EASAQUA WT 2102, EASAQUA X D 401, EASAQUA M 501, EASAQUA X D 803, EASAQUA M 502 and EASAQUA X L 600 (commercially available from Vencore X Chemical). Unsaturated isocyanate monomers include but are not limited to 2-acryloyloxyethylisocyanate (AOI), 2-methacryloyloxyethyl isocyanate (MOI), alpha, alpha-dimethyl meta-isopropenyl benzyl isocyanate (TMI), and the adduct of 2-hydroxyethyl acrylate (HEA) and IPDI in 1:1 ratio. A particularly suitable hydroxy functional alkyl polyurea formed from an isocyanurate is shown in Formula VII:

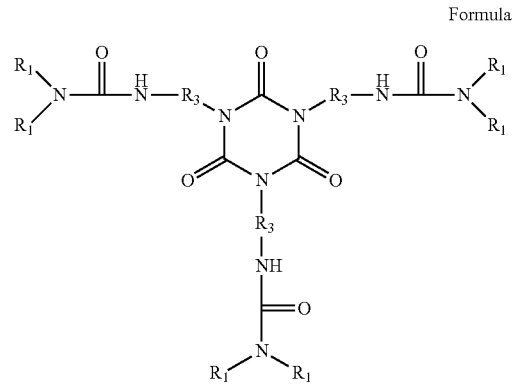

Formula VII wherein $R_1$ with reference to Formula VII is as described above; and each $R_3$ independently comprises an alkyl, aryl, alkylaryl, arylalkyl, alicyclic, and/or polyetheralkyl group.

A particularly suitable hydroxy functional alkyl polyurea formed from a bis-isocyanurate is shown below in Formula VIII:

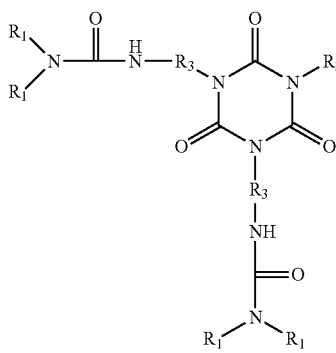
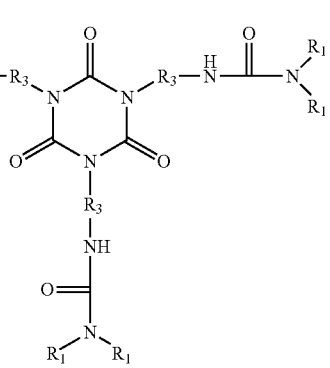

Formula VIII wherein $R_1$ and $R_3$ with reference to Formula VIII are as described above.

A biuret will be understood as referring to a compound that results upon the condensation of two molecules of urea, and is sometimes referred to as a carbamylurea. Biurets are commercial available from Vencore X Chemical and Covestro as, for example, DESMODUR N-75, DESMODUR N-100, and DESMODUR N-3200, HDB 75B, HDB 75M, HDB 75MX, HDB-LV. A particularly suitable hydroxy functional alkyl polyurea formed from a biuret is shown below in Formula IX:

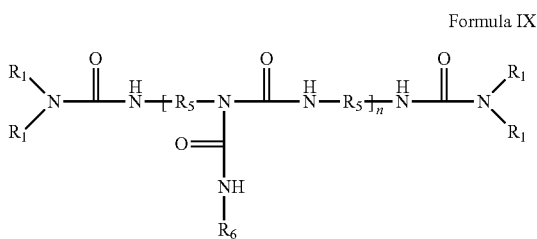

Formula IX wherein $R_1$ with reference to Formula IX is as described above; each $R_5$ independently comprises an alkyl, aryl, alkylaryl, arylalkyl, alicyclic, and/or polyetheralkyl group; and $R_6$ comprises H or an alkyl group.

Uretidione is a dimer of diisocyanate, examples of which include DESMODUR N-3400 polyisocyanate, a blend of the trimer and uretidione of HDI:

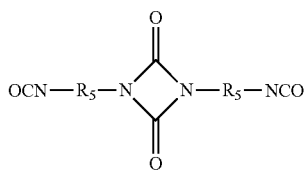

wherein each $R_5$ independently comprises an alkyl, aryl, alkylaryl, arylalkyl, alicyclic, and/or polyetheralkyl group.

An allophonate will be understood as referring to a compound made from urethane and isocyanate. A method for making an allophonate is described at Surface Coating, Vol 1, Raw material and their usage, Landon New York, Chapman and Hall, Page 106. The reaction is generally depicted below in scheme I:

Scheme I

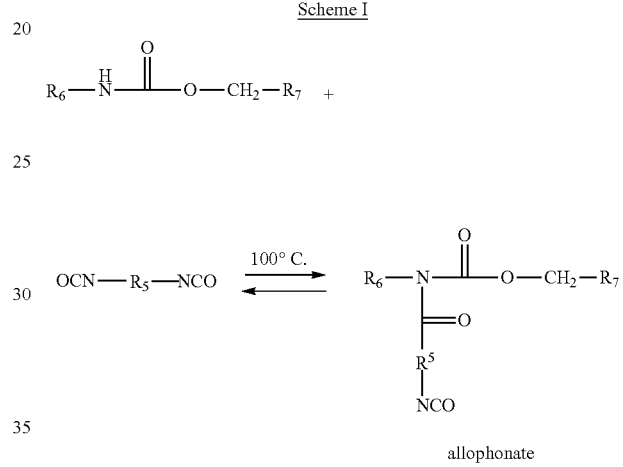

allophonate wherein $R_5$ and $R_6$ with reference to Scheme I are each as described above; and $R_7$ independently comprises the residue of a primary alcohol.

A glycoluril will be understood as referring to a compound composed of two cyclic urea groups joined across the same two-carbon chain, a suitable examples of which includes the below:

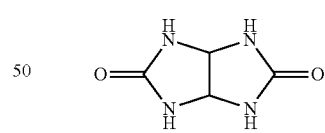

Glycoluril is widely commercially available, such as from Sigma-Aldrich. Benzoguanamine is also known as 6-phenyl-1,3,5-triazine-2,4-diamine and is commercially available from The Chemical Company, Jamestown, R.I.

A polyether amine will be understood as referring to a compound having one or more amine groups attached to a polyether backbone such as one characterized by propylene oxide, ethylene oxide, or mixed propylene oxide and ethylene oxide repeating units in their respective structures, such as, for example, one of the Jeffamine series products. Examples of such polyetheramines include aminated propoxylated pentaerythritols, such as JEFFAMINE XTJ-616, and those represented by Formulas (X) through (VI).

According to Formula (IV) the polyether amine may comprise:

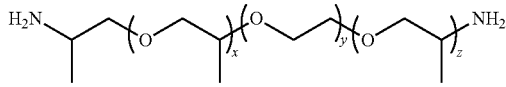

Formula X wherein y=0-39, x+z=1-68.

Suitable amine-containing compounds represented by Formula X include, but are not limited to, amine-terminated polyethylene glycol such as those commercially available from Huntsman Corporation in its JEFFAMINE ED series, such as JEFFAMINE HK-511, JEFFAMINE ED-600, JEFFAMINE ED-900 and JEFFAMINE ED-2003, and amine-terminated polypropylene glycol such as in its JEFFAMINE D series, such as JEFFAMINE D-230, JEFFAMINE D-400, JEFFAMINE D-2000 and JEFFAMINE D-4000.

According to Formula XI the polyetheramine may comprise:

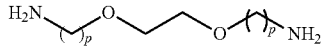

Formula XI wherein each p independently is 2 or 3.

Suitable amine-containing compounds represented by Formula XI include, but are not limited to, amine-terminated polyethylene glycol based diamines, such as Huntsman Corporation's JEFFAMINE EDR series, such as JEFFAMINE EDR-148 and JEFFAMINE EDR-176.

According to Formula XII the polyetheramine may comprise:

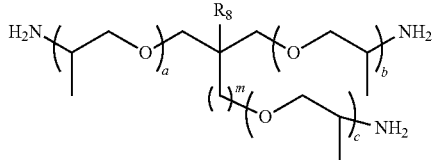

Formula XII wherein $R_8$ is H or $C_2H_5$, m=0 or 1, a+b+c=5-85.

Suitable amine-containing compounds represented by Formula (VI) include, but are not limited to, amine-terminated propoxylated trimethylolpropane or glycerol, such as Huntsman Corporation's Jeffamine T series, such as JEFFAMINE T-403, JEFFAMINE T-3000 and JEFFAMINE T-5000.

Particularly suitable are di- and tri- amines, such as 4,7,10-trioxa-1,13-tridecanediamine, JEFFAMINE D400, JEFFAMINE D4000, JEFFAMINE D2000, JEFFAMINE T403.

A "polymeric moiety" as used herein in the context of R or $R_2$ with reference to Formulas V to IX refers to any polymer or oligomer to which has been attached two to six hydroxy functional alkyl polyurea groups. The polymer can be, for example, a polyester polyurethane, a polyether polyurethane, or a polyamide polyurethane. The moiety can itself contain functionality, such as acid functionality, hydroxy functionality, and/or amine functionality. The polymeric moiety (which may be oligomeric as noted above) has an Mn of 500 or greater, such as 1000 or greater, 2500 or greater, 4000 or greater, or 5,000 or greater. Mn, as used herein, refers to the number average molecular weight and means the theoretical value as determined by Gel Permeation Chromatography using Waters 2695 separation module with a Waters 410 differential refractometer (RI detector) and polystyrene standards. The Mn values reported according to the invention were determined using this method. Tetrahydrofuran (THF) was used as the eluent at a flow rate of 1 ml $min^{-1}$, and two PL Gel Mixed C columns were used for separation.

In all cases, R and $R_2$ with reference to Formulas V to IX may be substituted or unsubstituted. $R_2$ with reference to Formulas V to IX, as noted above, may also comprise a substituted or unsubstituted $C_1$ to $C_{36}$ alkyl group and/or an aromatic group. For example, the alkyl group may have two to ten carbon atoms, such as six carbon atoms. The alkyl group may derive from an isocyanate, such as a diisocyanate. Suitable examples include isophorone diisocyanate and hexamethylene isocyanate. The aromatic group may derive from an aromatic ring containing isocyanate, suitable examples of which include methylene diphenyl diisocyanate, toluene diisocyanate and tetramethylxylylene diisocyanate.

Certain hydroxy functional alkyl polyureas of, and/or used according to, the invention may be made by reacting an isocyanate-containing compound with amino alcohol. Any isocyanate-containing compound having at least two isocyanate groups can be used, such as any of those described above. It will be appreciated that the "R" or "$R_2$" group with reference to Formulas V to IX will reflect the isocyanate-containing compound selected, if one is used.

Similarly, any amino alcohol having two or more carbon atoms can be used, and the "$R_1$" group with reference to Formulas V to IX will reflect the amino alcohol selected. The amino alcohol can have one, two or more hydroxyl functional groups. One or more amino alcohols can be used, which will result in different $R_1$ groups with reference to Formulas V to IX being present on the polyurea. $R_1$ with reference to Formulas V to IX can also be hydrogen or an alkyl group. Suitable amino alcohols include monoethanol amine, diethanol amine and diisopropanol amine.

The hydroxyl functional alkyl polyureas can be made by reacting amino alcohol with an isocyanate-containing compound in an organic polar solvent, such as alcohol or water. The equivalent ratio of amine to isocyanate may be 2-1:1-2, such as 1:1.

The hydroxy functional alkyl polyureas may be made by alternative methods as well. For example, amino alcohols can react with carbonate to form hydroxylalkyl carbamate, and hydroxylalkyl carbamate can further react with amines to form hydroxy functional alkyl polyureas.

The number-average molecular weight (Mn) of the hydroxy functional alkyl polyurea (even when the polyurea is in the form of a monomer or prepolymer, but not when R or $R_2$ with reference to Formulas V to IX is a polymeric moiety) may be 100 or greater, such as 350 or greater or 1,000 or greater, and/or can be 6,000 or lower, such as 3,000 or lower, or 2,000 or lower. The Mn of the hydroxy functional alkyl polyurea when R or $R_2$ with reference to Formulas V to IX is a polymeric moiety can be 500 or greater, such as 1,000 or greater, 5,000 or greater or 10,000 or greater.

It has surprisingly and advantageously been found by the present inventors that the hydroxyl alkyl urea functional materials typically cure at a lower temperature than, for example, hydroxyalkylamide material, such as a β-hydroxyalkylamide material.

The crosslinker may be in the form of a carbodiimide resin. The crosslinker may comprise a polycarbodiimide. Suitably, the crosslinker may comprise a polycarbodiimide having the following structural units (XIII) or (XIV) including mixtures thereof:

The active hydrogen-containing compound used in the preparation of the polycarbodiimide is suitably a chain extender or spacer linking polyisocyanates together to form NCO-adducts or to link NCO-functional polycarbodiimides together. Any suitable organic compound containing active hydrogens may be used. The term "active hydrogen atoms" refers to hydrogens which, because of their position in the molecule, display activity according to the Zerewitinoff test.

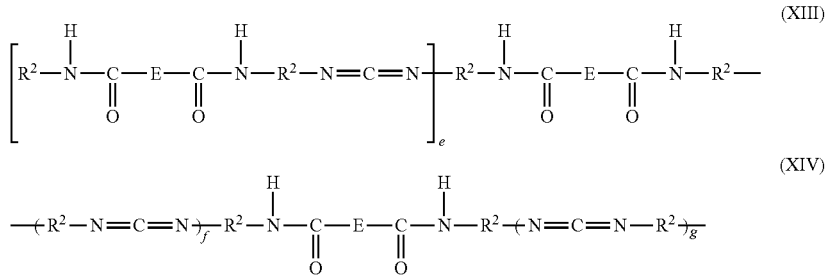

where e is an integer of from 2 to 20; f and g are each at least 1, and f+g is an integer up to 20; E is a radical selected from

 and

where $R^2$ with reference to structural units (XIII) or (XIV) comprises a cyclic radical and $R^3$ with reference to (XV) and (XVI) is a linear hydrocarbon radical containing at least 4 carbon atoms and $R^4$ with reference to (XVI) is hydrogen or an alkyl radical.

The polycarbodiimides may be prepared by reacting an organic group containing a polyisocyanate in the presence of a suitable catalyst to form a polycarbodiimide having terminal NCO-functionality, wherein an active hydrogen-containing compound is added before, during or after polycarbodiimide formation.

The polyisocyanate can be an aliphatic, including cycloaliphatic, or an aromatic polyisocyanate or mixture of the two. Aliphatic including cycloaliphatic polyisocyanates and alkaryl polyisocyanates are particularly suitable. The polyisocyanates can contain from 2 to 4, such as 2 isocyanate groups per molecule. Examples of suitable higher polyisocyanates are 1,2,4-benzene triisocyanate and polymethylene polyphenyl isocyanate. Examples of suitable aromatic diisocyanates are 4,4'-diphenylmethane diisocyanate, 1,3-phenylene diisocyanate, 1,4-phenylene diisocyanate and tolylene diisocyanate. Examples of suitable aliphatic diisocyanates are straight chain aliphatic diisocyanates such as 1,4-tetramethylene diisocyanate and 1,6-hexamethylene diisocyanate and alkaryl polyisocyanates such as m-tetramethylxylene diisocyanate. Also, cycloaliphatic diisocyanates can be employed. Examples include 1,4-cyclohexyl diisocyanate, isophorone diisocyanate, alpha, alpha-xylylene diisocyanate and 4,4-methylene-bis(cyclohexyl isocyanate). Substituted organic group-containing polyisocyanates can also be used in which the substituents are nitro, chloro, alkoxy and other groups that are not reactive with hydroxyl groups or active hydrogens and provided the substituents are not positioned to render the isocyanate group unreactive.

Accordingly, active hydrogens include hydrogen atoms attached to oxygen or nitrogen, and thus useful compounds will include those having at least two of these groups (in any combination):

—OH, and —NH$_2$

The moieties attached to each group can be aliphatic, including cycloaliphatic, aromatic, or of a mixed type with aliphatic being particularly suitable.

The active hydrogen-containing material can contain from 2 to 4, particularly suitable 2 active hydrogens per molecule.

Examples of such compounds include amines, which includes polyamines, aminoalcohols, mercapto-terminated derivatives, and alcohols that includes polyhydroxy materials (polyols) that are particularly suitable because of the ease of reaction with polyisocyanates. Also polyols generally give no side reactions, giving higher yields of urethane product with no by-product and the products are hydrolytically stable. Also, with regard to polyols, there are a wide variety of materials available which can be selected to give a wide spectrum of desired properties. In addition, the polyols have desirable reaction rates with polyisocyanates. Both saturated and unsaturated active hydrogen-containing compounds can be used, but saturated materials are particularly suitable because of superior coating properties.

The polyhydroxyl materials or polyols can be either low or high molecular weight materials and in general will have average hydroxyl values as determined by ASTM designation E-222-67, Method B, of 2000 and below, such as between 2000 and 10. The term "polyol" is meant to include materials having an average of two or more hydroxyl groups per molecule.

The polyols include low molecular weight diols, triols and higher molecular weight polyols, low molecular weight amide-containing polyols and higher polymeric polyols such as polyester polyols, polyether polyols, polycarbonate polyols and hydroxy-containing (meth)acrylic polymers. The polymers typically have hydroxyl values of from 10 to 180. Also, the polymers typically have number average molecular weights of 96 to 10,000 Da.

The low molecular weight diols, triols and higher alcohols useful in the instant invention are known in the art. They have hydroxy values of 200 or above, usually within the range of 200 to 2000. Such materials include aliphatic polyols, particularly alkylene polyols containing from 4 to 18 carbon atoms. Examples include 1,4-butanediol and 1,6-hexanediol. Also useful are polyols containing ether linkages such as diethylene glycol and tetraethylene glycol.

To form the polycarbodiimide, the polyisocyanate with or without the active hydrogen-containing compound may be condensed with the elimination of carbon dioxide to form the polycarbodiimide, that is, a polymer containing [N=C=N]$_n$ units where n with reference to the [N=C=N] =2 to 20, such as 2 to 10.

The condensation reaction is typically conducted by taking the solution of the polyisocyanate and heating in the presence of suitable catalyst. Examples of catalyst include 1-ethyl-3-phospholine, 1-ethyl-3-methyl-3-phospholine-1-oxide, 1-ethyl-3-methyl-3-phospholine-1-sulfide, 1-ethyl-3-methyl-phospholidine, 1-ethyl-3-methyl-phospholidine-1-oxide, 3-methyl-1-phenyl-3-phospholine-1-oxide and bicyclic terpene alkyl or hydrocarbyl aryl phosphine oxide or camphene phenyl phosphine oxide.

The particular amount of catalyst used will depend to a large extent on the reactivity of the catalyst itself and the polyisocyanate being used. A concentration range of 0.05-5 parts of catalyst per 100 parts of adduct is generally suitable.

The resulting polycarbodiimide has terminal NCO groups that can then be reacted with an active hydrogen-containing hydrophilic compound.

The hydrophilic compound may be a polyether alcohol or polyether amine or mixtures thereof having a polyether backbone, typically based on ethylene oxide or mixed ethylene oxide and propylene and having a molecular weight greater than 500, such as at least 1000 on a number average basis. Typical alcohols and amines have the following structural formula:

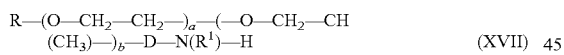

or

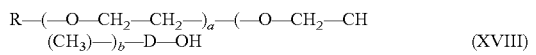

where R with reference to formulas (XVII) and (XVIII) is $C_1$ to $C_4$ alkyl; a with reference to formulas (XVII) and (XVIII) is 5 to 50 and b with reference to formulas (XVII) and (XVIII) is 0 to 35, and when b with reference to formulas (XVII) and (XVIII) is present the mole ratio of a to b with reference to formulas (XVII) and (XVIII) is at least 1:1; $R^1$ with reference to formula (XVIII) is hydrogen or a hydrocarbon radical and D with reference to formulas (XVII) and (XVIII) is a divalent linking group or a chemical bond.

Reaction of the polyether alcohol or amine with the NCO-containing carbodiimide may be conducted with a stoichiometric equivalent of amine to NCO equivalents or a slight excess of alcohol or amine and at a temperature typically from 80 to 110° C. until an IR spectrum of the reaction mixture indicates substantially no remaining NCO functionality.

Depending on when the active hydrogen chain extender or spacer is used in the reaction, the polycarbodiimide has a structure such that each carbodiimide unit or polycarbodiimide unit is attached to a unit selected from urethane, thiourethane urea, thiourea and a hydrophilic unit occurs at one or terminal positions of the polycarbodiimide via a urethane or urea linkage.

Typically, the polycarbodiimide has a weight average molecular weight of 2600 to 12,000, such as 3000 to 10,000, and a diimide equivalent weight (number average molecular weight/number of carbodiimide groups) of at least 600, such as 600 to 2000.

When the active hydrogen chain extender is added before or during polycarbodiimide formation, that is, is used to chain extend a polyisocyanate to form an NCO-adduct, the polycarbodiimide can be represented from the following structural formula when the polyisocyanate and the active hydrogen-containing compound are difunctional:

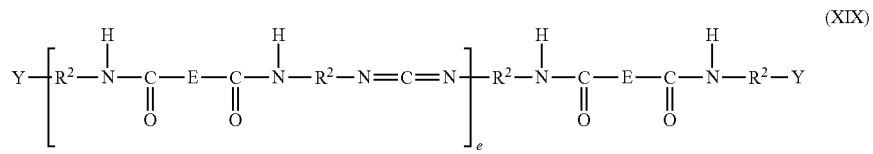 (XIX)

where e with reference to formula (XIX) is an integer of from 2 to 20, such as 2 to 10; E with reference to formula (XIX) is a radical selected from

 (XX)

 (XXI)

where $R^2$ with reference to formula (XIX) is a cyclic radical such as a cycloaliphatic or an alkaryl radical that may contain 6 to 20 carbon atoms such as those of the structure:

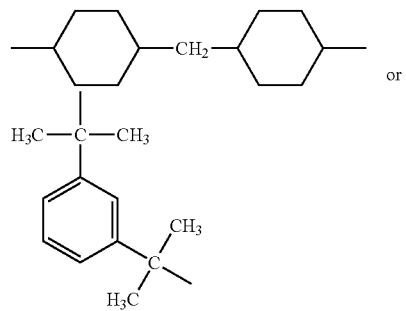

$R^3$ with reference to formula (XX) and (XXI) is a linear hydrocarbon radical optionally including hetero atoms containing at least 4 carbon atoms such as a polyethylene group having a number average molecular weight of 96 to 10,000. $R^4$ with reference to formula (XXI) is hydrogen or a hydrocarbon radical such as alkyl containing from 1 to 4 carbon atoms. Y with reference to formula (XIX) is a radical of the structure:

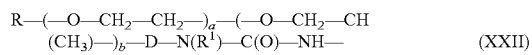 (XXII)

or

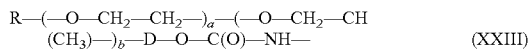

(XXIII)

where R with reference to formula (XXII) and (XXIII) is $C_1$ to $C_4$ alkyl; a with reference to formula (XXII) and (XXIII) is 5 to 50 and b with reference to formula (XXII) and (XXIII) is 0 to 35, and when b with reference to formulas (XXII) and (XXIII) is present the mole ratio of a to b with reference to formulas (XXII) and (XXIII) is at least 1:1; $R^1$ with reference to formula (XXII) is hydrogen or a hydrocarbon radical and D with reference to formula (XXII) and (XXIII) is a divalent linking group or a chemical bond.

When the active hydrogen chain extender is added after polycarbodiimide formation, that is, is used to chain extend an NCO-functional polycarbodiimide, the polycarbodiimide can be represented from the following structural formula when the NCO-functional polycarbodiimide and the active hydrogen-containing compound are difunctional.

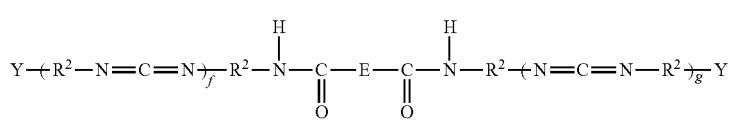

(XXIV)

where f and g with reference to formula (XXIV) are each at least 1, and f+g with reference to formula (XXIV) is an integer up to 20 such as up to 10; E with reference to formula (XXIV) is a radical selected from

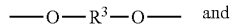 and (XXV)

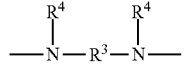 (XXVI)

where $R^2$, $R^3$, $R^4$ and Y with reference to formulas (XXIV), (XXV) and (XXVI) have the meanings mentioned above for (XIX).

Organic solvent can optionally be present in the synthesis of the polycarbodiimide. Polar water miscible solvents such as N-methyl pyrrolidone can be used in amounts of about 5-25 percent by weight based on weight of the reaction mixture.

The powder coating composition may comprise any suitable weight ratio of acid functional polyester material (a) to crosslinker (b). The powder coating composition may have a weight ratio of (a) to (b) from to 50:1 to 1:1, suitably from 25:1 to 1:1, such as from 20:1 to 5:1, or even from 15:1 to 5:1. Suitably, the powder coating composition may have a weight ratio of (a) to (b) of 10:1.

The powder coating composition of the present invention may have any suitable average particle size ($D_{50}$). The powder coating composition may have an average particle size from 5 to 300 microns (μm), suitably from 5 to 150 μm, such as from 10 to 75 μm, or even from 10 to 50 μm. Particles having these sizes may be produced by any suitable method. Suitable methods will be well known to a person skilled in the art. Examples of suitable methods include, but are not limited to, cold grinding and sieving methods.

The average particle size ($D_{50}$) may be measured by any suitable method. Suitable methods will be well known to a person skilled in the art. The average particle size ($D_{50}$) may be measured using laser diffraction analysis. Suitably, the laser diffraction analysis may be performed using a Microtrac S3000 laser diffraction analyser (commercially available from Microtrac), suitably according to the manufacturer's protocol. All values for average particle size ($D_{50}$) reported herein were measured this way.

The powder coating compositions of the present invention may comprise any suitable amount of thermoset resin. The powder coating composition may comprise from 1 to 90 wt %, suitably from 2 to 70 wt %, such as from 5 to 50 wt %, of the thermoset resin based on the total solid weight of the coating composition.

The thermoset resin may comprise any suitable amount of acid functional polyester material. The thermoset resin may comprise up to 50 wt %, suitably up to 75 wt %, such as up to 90 wt % or even up to 100 wt % acid functional polyester material based on the total solid weight of the thermoset resin.

The powder coating compositions of the present invention may comprise any suitable amount of acid functional polyester material. The powder coating composition may comprise from 1 to 90 wt %, suitably from 2 to 70 wt %, such as from 5 to 50 wt % of the acid functional polyester material based on the total solid weight of the coating composition.

The powder coating compositions of the present invention may comprise any suitable amount of thermoplastic resin. The powder coating composition may comprise from 1 to 90 wt %, suitably from 10 to 80 wt %, such as from 10 to 75 wt %, or even from 20 to 50 wt % of the acid functional polyester material based on the total solid weight of the coating composition.

The powder coating compositions may comprise any suitable amount of crosslinker. The powder coating compositions may comprise from 0.5 to 50 wt %, suitably from 1 to 40 wt %, such as from 2 to 30 wt %, or even from 5 to 20 wt % of the crosslinker based on the total solid weight of the coating composition. Suitably, the powder coating compositions may comprise from 5 to 10 wt % of the crosslinker based on the total solid weight of the coating composition.

The powder coating compositions may comprise less than 7 wt %, suitably less than 6 wt % of the crosslinker based on the total solid weight of the coating composition. The powder coating compositions may comprise from 0.5 to 7 wt %, suitably from 1 to 7 wt %, such as from 2 to 7 wt %, or even from 5 to 7 wt % of the crosslinker based on the total solid weight of the coating composition. The powder coating compositions may comprise from 0.5 to 6 wt %, suitably from 1 to 6 wt %, such as from 2 to 6 wt %, or even from 5 to 6 wt % of the crosslinker based on the total solid weight of the coating composition.

Suitably, the powder coating compositions may comprise less than 6 wt % of the crosslinker based on the total solid weight of the coating composition.

It has surprisingly and advantageously been found by the present inventors that a lower amount of crosslinker may be used in the powder coating compositions of the present invention compared to the amounts that are typically used in powders of the prior art. In particular, it has surprisingly and advantageously been found by the present inventors that a lower amount of β-hydroxyalkylamide material may be used in the powder coating compositions of the present invention compared to the amounts that are typically used in powders of the prior art.

The powder coating compositions may further comprise one or more pigment and/or filler. The powder coating composition may comprise a single pigment or filler or a mixture of pigments and/or fillers. Suitable pigments include, but are not limited to, the following: titanium dioxide; ultramarine blue; phthalocyanines, such as phthalocyanine blue and phthalocyanine green; anthraquinones; quinacridones; thioindigos; carbon black; graphite fibrils; iron oxides, such as black iron oxide; chromium green oxide; ferried yellow; quindo red; or combinations thereof. Suitable fillers include, but are not limited to, the following: barium sulphate; silicas, such as precipitated silicas and clay; or combinations thereof.

Suitably, the powder coating composition may comprise titanium dioxide, barium sulphate or a combination thereof. Suitably, the powder coating composition may comprise titanium dioxide and barium sulphate.

The pigment and/or filler, when present, may be used in the powder coating compositions in any suitable amount. The pigment and/or filler, when present, may be used in the powder coating composition in amounts of at least 10 wt % based on the total solid weight of the coating composition. The powder coating composition may comprise from 10 to 90 wt %, suitably from 10 to 80 wt %, such as from 10 to 70 wt %, or even from 10 to 50 wt % of pigment and/or filler based on the total solid weight of the powder coating composition. The powder coating composition may comprise from 15 to 90 wt %, suitably from 15 to 80 wt %, such as from 15 to 70 wt %, or even from 15 to 50 wt % of pigment and/or filler based on the total solid weight of the coating composition. The powder coating composition may comprise from 20 to 90 wt %, suitably from 20 to 80 wt %, such as from 20 to 70 wt %, or even from 20 to 50 wt % of pigment and/or filler based on the total solid weight of the powder coating composition.

The powder coating composition may further comprise one or more curing catalyst. The powder coating compositions may comprise any curing agent suitable to catalyse the reaction between the acid functional polyester material and the β-hydroxyalkylamide crosslinker. Suitable curing catalysts will be well known to a person skilled in the art. Examples of suitable curing catalysts include, but are not limited to, the following: organic tin compounds, such as tin (II) salts of carboxylic acids, for example, tin (II) acetate, tin (II) octonoate, tin (II) ethylhexanoate and tin (II) laurate, tin (IV) compounds, for example, dibutyltin oxide, dibutyltin dichloride, dibutyltin diacetate, dibutyltin dilaurate, dibutyltin maleate and dioctyltin diacetate; tertiary amines, such as diazabicyclo[2.2.2]octane and 1,5-diazabicyclo[4.3.0]non-5-ene; and combinations thereof.

The powder coating compositions of the present invention may optionally comprise a further additive or combination of additives. The powder coating composition may optionally comprise any suitable additive or combination of additives. Suitable additives will be well known to the person skilled in the art. Examples of suitable additives include, but are not limited to the following: lubricants; diluents; plasticisers; surfactants; stabilising agents; flow control agents; thixotropic agents; and combinations thereof.

Suitable lubricants will be well known to the person skilled in the art. Suitable examples of lubricants include, but are not limited to one or more of the following: carnauba wax and polyethylene type lubricants. The lubricant, when present, may be used in the thermoset powder coating composition in amounts of at least 0.01 wt % based on the total solid weight of the powder coating composition.

Surfactants may optionally be added to the powder coating composition in order to aid in flow and wetting of the substrate. Suitable surfactants will be well known to the person skilled in the art. It will be appreciated by a person skilled in the art that when the thermoset powder coating composition is to be used in food and/or beverage container applications, the surfactant, when present, is chosen to be compatible with such applications. Suitable surfactants include, but are not limited to one or more of the following: alkyl sulphates (e.g., sodium lauryl sulphate); ether sulphates; phosphate esters; sulphonates; and their various alkali, ammonium, amine salts; aliphatic alcohol ethoxylates; alkyl phenol ethoxylates (e.g. nonyl phenol polyether); salts and/or combinations thereof. The surfactants, when present, may be present in amounts from 0.01 to 10 wt % based on the total solid weight of the powder coating composition.

Suitable flow control agents will be well known to a person skilled in the art. Suitable flow control agents include, but are not limited to, the following: acrylate polymers, such as polylauryl acrylate, polybutyl acrylate, poly(2-ethylhexyl) acrylate, poly(ethyl-2-ethylhexyl) acrylate, polylauryl methacrylate and polyisodecenyl methacrylate; fluorinated polymers, such as an ester of polyethylene glycol or polypropylene glycol and fluorinated fatty acids, for example, an ester of polyethylene glycol of a molecular weight of over 2,500 Da and perfluorooctanoic acid; polymeric siloxanes, such as polymeric siloxanes of a molecular weight of over 1,000 Da, for example, poly(dimethylsiloxane) and poly(methylphenylsiloxane); and combinations thereof. The flow control agents, when present, may be present in amounts from 0.01 to 10 wt %, suitably from 0.1 to 5 wt %, such as from 0.5 to 4 wt %, or even from 1 to 3 wt % based on the total solid weight of the powder coating composition. It will be appreciated by a person skilled in the art that the flow controls agents, when present, must be suitable for use in a powder composition.

The powder coating compositions according to the present invention are substantially free of bisphenol A (BPA) and derivatives thereof. The powder coating compositions may be essentially free or may be completely free of bisphenol A (BPA) and derivatives thereof. Derivatives of bisphenol A include, for example, bisphenol A diglycidyl ether (BADGE). The powder coating compositions according to the present invention are also substantially free of bisphenol F (BBF) and derivatives thereof. The powder coating compositions may be essentially free or may be completely free of bisphenol F (BPF) and derivatives thereof. Derivatives of bisphenol F include, for example, bisphenol F diglycidyl ether (BPFG). The compounds or derivatives thereof mentioned above may not be added to the composition intentionally but may be present in trace amounts because of unavoidable contamination from the environment. "Substantially free" refers to powder coating compositions, or components thereof, containing less than 1000 parts per million (ppm) of any of the compounds or derivatives thereof mentioned above. "Essentially free" refers to powder coating compositions, or components thereof, containing less than 100 ppm of any of the compounds or derivatives thereof mentioned above. "Completely free" refers to powder coating compositions, or components thereof, containing less than 20 parts per billion (ppb) of any of the compounds or derivatives thereof mentioned above.

The powder coating compositions of the present invention may be substantially free, may be essentially fee or may be completely free of dialkyltin compounds, including oxides or other derivatives thereof. Examples of dialkyltin compounds include, but are not limited to one or more of the following: dibutyltindilaurate (DBTDL); dioctyltindilaurate; dimethyltin oxide; diethyltin oxide; dipropyltin oxide; dibutyltin oxide (DBTO); dioctyltinoxide (DOTO) or combinations thereof. "Substantially free" refers to powder coating compositions, or components thereof, containing less than 1000 parts per million (ppm) of any of the compounds or derivatives thereof mentioned above. "Essentially free" refers to powder coating compositions, or components thereof, containing less than 100 ppm of any of the compounds or derivatives thereof mentioned above. "Completely free" refers to powder coating compositions, or components thereof, containing less than 20 parts per billion (ppb) of any of the compounds or derivatives thereof mentioned above.

The powder coating compositions of the present invention may be substantially free, may be essentially fee or may be completely free of formaldehyde or sources thereof. "Substantially free" refers to powder coating compositions, or components thereof, containing less than 1000 parts per million (ppm) formaldehyde or sources thereof mentioned above. "Essentially free" refers to powder coating compositions, or components thereof, containing less than 100 ppm formaldehyde or sources thereof mentioned above. "Completely free" refers to powder coating compositions, or components thereof, containing less than 20 parts per billion (ppb) formaldehyde or sources thereof.

It will be appreciated by a person skilled in the art that the crosslinking material, when present, may be selected so as to be substantially free, essentially fee or completely free of formaldehyde or sources thereof.

The powder coating compositions of the present invention may be substantially free, may be essentially free or may be completely free of bromine. "Substantially free" refers to powder coating compositions, or components thereof, containing less than 1000 parts per million (ppm) of bromine. "Essentially free" refers to powder coating compositions, or components thereof, containing less than 100 ppm of bromine. "Completely free" refers to powder coating compositions, or components thereof, containing less than 20 parts per billion (ppb) of bromine.

The powder coating compositions of the present invention may be substantially free, may be essentially free or may be completely free of solvent. "Substantially free" refers to powder coating compositions, or components thereof, containing less than 1000 parts per million (ppm) of solvent. "Essentially free" refers to powder coating compositions, or components thereof, containing less than 100 ppm of solvent. "Completely free" refers to powder coating compositions, or components thereof, containing less than 20 parts per billion (ppb) of solvent.

The powder coating composition of the present invention may be prepared by any suitable method. For example, the powder coating composition may be prepared by first dry blending the thermoset resin comprising an acid functional polyester material, the thermoplastic resin, the crosslinker material and, if present, pigment and/or filler, curing agent and additives in a blender. The blender may be operated for any suitable period of time. Suitably, the blender may be operated for a period of time sufficient to result in a homogeneous dry blend of the materials charged thereto. The homogenous dry blend may then be melt blended in an extruder, such as a twin-screw co-rotating extruder, operated within a temperature range from 80 to 140° C., suitably from 100 to 125° C. The extrudate of the thermoset powder may be cooled and is typically milled to an average particle size as described above.

The powder coating composition may be prepared by first dispersing the thermoset resin comprising an acid functional polyester material (a), the thermoplastic resin (b), crosslinker material (c) and, if present, pigment and/or filler and additives in a liquid carrier. The dispersion may then be dried to form a powder. The dispersion may be dried to a powder by any suitable method, such as spray drying, drying on heated plates, microwave drying, drum drying or any know method of evaporation techniques. The dried powder may then be ground or milled to an average particle size as described above.

Thus, according to a second aspect of the present invention there is provided a method for producing a powder coating composition comprising:
 a) a thermoset resin comprising an acid functional polyester material,
 b) a thermoplastic resin and
 c) a crosslinker material,
the method comprising the steps of:
 i) dispersing components (a), (b) and (c) in a liquid carrier,
 ii) drying the dispersion of step (i) to form a powder, and
 iii) grinding the powder of step (ii) to a particle size of 5 to 300 micron (μm),
wherein the coating composition is substantially free of bisphenol A (BPA), bisphenol F (BPF), bisphenol A diglycidyl ether (BADGE) and bisphenol F diglycidyl ether (BFDGE).

The liquid carrier may comprise water, an organic solvent, a mixture of water and one or more organic solvent(s) or a mixture of organic solvents. Suitably, the liquid carrier may comprise water. The liquid carrier may be present in the form of a dispersion of the thermoplastic resin as described above.

Suitable organic solvents include, but are not limited to one or more of the following: aliphatic hydrocarbons such as mineral spirits and high flash point naphtha; aromatic hydrocarbons such as benzene; toluene; xylene; solvent naphtha 100, 150, 200; those available from Exxon-Mobil Chemical Company under the SOLVESSO trade name; alcohols such as ethanol; n-propanol; isopropanol; and n-butanol; ketones such as acetone; cyclohexanone; methylisobutyl ketone; methyl ethyl ketone; esters such as ethyl acetate; butyl acetate; n-hexyl acetate; glycols such as butyl glycol; glycol ethers such as methoxypropanol; ethylene glycol monomethyl ether; ethylene glycol monobutyl ether and combinations thereof.

It will be appreciated by a person skilled in the art that, when the thermoplastic resin is provided in the form of a dispersion, some or all of the liquid carrier of step (i) of the second aspect of the present invention may be present in the form of the liquid carrier of the thermoplastic resin dispersion.

It will be appreciated by a person skilled in the art that when the crosslinker material is provided in the form of a dispersion, some or all of the liquid carrier of step (i) of the second aspect of the present invention may be present in the form of the liquid carrier of the crosslinker material dispersion. For example, when the crosslinker material is a polycarbodiimide material and is provided in the form of a dispersion, some or all of the liquid carrier of step (i) of the second aspect of the present invention may be present in the form of the liquid carrier of the crosslinker material dispersion.

It has surprisingly and advantageously found by the present inventors that the method according to the second aspect of the present invention enables both thermosetting and thermoplastic resins to be included in a coating composition. Typically, these two types of resins are incompatible, as would be well known to a person skilled in the art.

The powder coating composition of the present invention is a curable coating composition. "Curable coating compositions" and like terms as used herein, refers to coating compositions that have an initial powder state and a final state in which the coating composition has been transformed into a substantially continuous, coalesced state.

The powder coating composition of the present invention may be cured by any suitable method. The powder coating composition may be cured by heat curing or by chemical curing, suitably by heat curing. The powder coating composition, when heat cured, may be cured at any suitable temperature. The powder coating composition, when heat cured, may be cured at temperatures from 50 to 350° C., suitably from 100 to 320° C., such as from 150 to 300° C., or even from 200 to 300° C.

The powder coating composition according to the first aspect of the present invention may be applied to any suitable substrate. The powder coating composition may be applied to a metal substrate. Examples of suitable metal substrates include, but are not limited to, food and/or beverage packaging, components used to fabricate such packaging or monobloc aerosol cans and/or tubes. Suitably, the food and/or beverage packaging may be a can. Examples of cans include, but are not limited to one or more of the following, two-piece cans, three-piece cans and the like. Suitable examples of monobloc aerosol cans and/or tubes include, but are not limited to, deodorant and hair spray containers. Monobloc aerosol cans and/or tubes may be aluminium monobloc aerosol cans and/or tubes.

The powder coating compositions may be applied to food and/or beverage packaging or components used to fabricate such packaging.

The powder coating compositions may be applied to monobloc aerosol cans and/or tubes.

The application of various pre-treatments and coatings to packaging is well established. Such treatments and/or coatings, for example, can be used in the case of metal cans, wherein the treatment and/or coating is used to retard or inhibit corrosion, provide a decorative coating, provide ease of handling during the manufacturing process, and the like. Coatings can be applied to the interior of such cans to prevent the contents from contacting the metal of the container. Contact between the metal and a food or beverage, for example, can lead to corrosion of a metal container, which can then contaminate the food or beverage. This is particularly true when the contents of the can are acidic in nature. The coatings applied to the interior of metal cans also help prevent corrosion in the headspace of the cans, which is the area between the fill line of the product and the can lid; corrosion in the headspace is particularly problematic with food products having a high salt content. Coatings can also be applied to the exterior of metal cans. Certain powder coatings of the present invention are particularly applicable for use with coiled metal stock, such as the coiled metal stock from which the ends of cans are made ("can end stock"), and end caps and closures are made ("cap/closure stock"). Since coatings designed for use on can end stock and cap/closure stock are typically applied prior to the piece being cut and stamped out of the coiled metal stock, they are typically flexible and extensible. For example, such stock is typically coated on both sides. Thereafter, the coated metal stock is punched. For can ends, the metal is then scored for the "pop-top" opening and the pop-top ring is then attached with a pin that is separately fabricated. The end is then attached to the can body by an edge rolling process. A similar procedure is done for "easy open" can ends. For easy open can ends, a score substantially around the perimeter of the lid allows for easy opening or removing of the lid from the can, typically by means of a pull tab. For caps and closures, the cap/closure stock is typically coated, such as by roll coating, and the cap or closure stamped out of the stock; it is possible, however, to coat the cap/closure after formation. Coatings for cans subjected to relatively stringent temperature and/or pressure requirements should also be resistant to popping, corrosion, blushing and/or blistering.

Accordingly, the present invention is further directed to a package coated at least in part with any of the powder coating compositions described above. A "package" is anything used to contain another item, particularly for shipping from a point of manufacture to a consumer, and for subsequent storage by a consumer. A package will be therefore understood as something that is sealed so as to keep its contents free from deterioration until opened by a consumer. The manufacturer will often identify the length of time during which the food or beverage will be free from spoilage, which typically ranges from several months to years. Thus, the present "package" is distinguished from a storage container or bakeware in which a consumer might make and/or store food; such a container would only maintain the freshness or integrity of the food item for a relatively short period. A package according to the present invention can be made of metal or non-metal, for example, plastic or laminate, and be in any form. An example of a suitable package is a laminate tube. Another example of a suitable package is metal can. The term "metal can" includes any type of metal can, container or any type of receptacle or portion thereof that is sealed by the food and/or beverage manufacturer to minimize or eliminate spoilage of the contents until such package is opened by the consumer. One example of a metal can is a food can; the term "food can(s)" is used herein to refer to cans, containers or any type of receptacle or portion thereof used to hold any type of food and/or beverage. The term "metal can(s)" specifically includes food cans and also specifically includes "can ends" including "E-Z open ends", which are typically stamped from can end stock and used in conjunction with the packaging of food and beverages. The term "metal cans" also specifically includes metal caps and/or closures such as bottle caps, screw top caps and lids of any size, lug caps, and the like. The metal cans can be used to hold other items as well, including, but not limited to, personal care products, bug spray, spray paint, and any other compound suitable for packaging in an aerosol can. The cans can include "two piece cans" and "three-piece cans" as well as drawn and ironed one-piece cans; such one piece cans often find application with aerosol products. Packages coated according to the present invention can also include plastic bottles, plastic tubes, laminates and flexible packaging, such as those made from PE, PP, PET and the like. Such packaging could hold, for example, food, toothpaste, personal care products and the like.

The powder coating can be applied to the interior and/or the exterior of the package. The powder coating could also be applied as a rim coat to the bottom of the can. The rim coat functions to reduce friction for improved handling during the continued fabrication and/or processing of the can. The powder coating can also be applied to caps and/or closures; such application can include, for example, a protective varnish that is applied before and/or after formation of the cap/closure and/or a pigmented enamel post applied to the cap, particularly those having a scored seam at the bottom of the cap. Decorated can stock can also be partially coated externally with the coating described herein, and the decorated, coated can stock used to form various metal cans.

Metal coils, having wide application in many industries, are also substrates that can be coated according to the present invention. Coil coatings also typically comprise a colorant.

The powder coating composition according to the first aspect of the present invention may be applied to at least a portion of the metal substrate. For example, when the powder coating composition is applied to a monobloc aerosol tube and/or can, the powder coating composition may be applied to at least a portion of an internal surface of said tube and/or can.

The powder coating compositions according to the first aspect of the present invention may be applied to the metal substrate by any suitable method. Methods of applying said powder coating compositions to the metal substrate will be well known to a person skilled in the art. Suitable application methods include, but are not limited to one or more of the following: spray coating; roll coating; dipping; and electrocoating such as, for example, ultra corona discharge. Suitably, the powder coating compositions according to the present invention may be applied to the monobloc aerosol can by ultra corona discharge.

When the substrate is electrically conductive, the powder coating composition is typically electrostatically applied. Electrostatic spray application generally involves drawing the powder coating composition from a fluidized bed and propelling it through a corona field. The particles of the powder coating composition become charged as they pass through the corona field and are attracted to and deposited upon the electrically conductive substrate, which is grounded. As the charged particles begin to build up, the substrate becomes insulated, thus limiting further particle deposition. This insulating phenomenon typically limits the film build of the deposited coating composition to a maximum of 250 to 300 µm (microns), in some cases, 75 to 150 µm.

The powder coating compositions according to the present invention may be applied to the metal substrate to any suitable dry film thickness. The powder coating compositions according to the first aspect of the present invention may be applied to the metal substrate to a dry film thickness from 0.1 µm (microns) to 300 µm, suitably from 3 µm to 250 µm, such as from 5 µm to 150 µm, or even from 5 µm to 75 µm, such as from 10 µm to 25 µm.

The powder coating composition according to the present invention may be applied to the metal substrate as a single layer or as part of a multi layer system. The powder coating compositions according to the first aspect of the present invention may be applied to the metal substrate as a single layer. The powder coating compositions according to the first aspect of the present invention may be applied to the metal substrate as the first coat of a multi coat system. Suitably, the powder coating compositions according to the first aspect of the present may be applied to the metal substrate as an undercoat or a primer. The second, third, fourth etc. coats may comprise any suitable paint such as those containing, for example, epoxy resins; polyester resins; polyurethane resins; polysiloxane resins; hydrocarbon resins or combinations thereof. The powder coating compositions according to the first aspect of the present invention may be applied on top of another paint layer as part of a multi layer system. For example, the powder coating compositions of the first aspect of the present invention may be applied on top of a primer. The powder coating compositions according to the first aspect of the present invention may form an intermediate layer or a top coat layer. The powder coating compositions according to the present invention may be applied to the metal substrate once or multiple times. Any or all of the layers may be substantially free, essentially free or completely free of BPA, BPF and derivatives thereof.

According to a further aspect of the present invention there is provided a metal substrate coated on at least a portion thereof with a powder coating composition, the powder coating composition comprising:

a) a thermoset resin comprising an acid functional polyester material, b) a thermoplastic resin and c) a crosslinker, wherein the coating composition is substantially free of bisphenol A (BPA), bisphenol F (BPF), bisphenol A diglycidyl ether (BADGE) and bisphenol F diglycidyl ether (BFDGE).

According to a further aspect of the present invention there is provided food and/or beverage packaging coated on at least a portion thereof with a powder coating composition, the powder coating composition comprising:

a) a thermoset resin comprising an acid functional polyester material, b) a thermoplastic resin and c) a crosslinker, wherein the coating composition is substantially free of bisphenol A (BPA), bisphenol F (BPF), bisphenol A diglycidyl ether (BADGE) and bisphenol F diglycidyl ether (BFDGE).

According to a further aspect of the present invention there is provided a monobloc aerosol can and/or tube coated on at least a portion thereof with a powder coating composition, the powder coating composition comprising:

a) a thermoset resin comprising an acid functional polyester material, b) a thermoplastic resin and c) a crosslinker, wherein the coating composition is substantially free of bisphenol A (BPA), bisphenol F (BPF), bisphenol A diglycidyl ether (BADGE) and bisphenol F diglycidyl ether (BFDGE).

All of the features contained herein may be combined with any of the above aspects and in any combination.

For a better understanding of the invention, and to show how embodiments of the same may be carried into effect, reference will now be made, by way of example, to the following experimental data.

EXAMPLES

Coating Composition 1

Coating composition 1, containing a thermosetting resin and two thermoplastic resins, was prepared according to the formulation in Table 1 and dried using an appropriate method. All amounts in Table 1 are given in parts by weight (pbw).

TABLE 1

Coating Composition 1

| | Coating Composition 1 |
|---|---|
| Thermoplastic resin 1 [1] | 24.57 |
| Thermoplastic resin 2 [2] | 49.14 |
| Thermoset resin [3] | 11.60 |
| Crosslinker [4] | 4.25 |
| Pigment 1 [5] | 2.46 |
| Pigment 2 [6] | 0.01 |
| Filler [7] | 4.80 |
| Additive 1 [8] | 0.24 |
| Additive 2 [9] | 0.09 |
| Additive 3 [10] | 2.83 |
| Total | 100.00 |

[1] Acrylic dispersion (Acrylic dispersion with acid number 30, Mw of 10 k to 30 k; 30% solid dispersed in 70% water)
[2] Polyolefin dispersion (Polymeric dispersion from Michelman Products, ME 310)
[3] Acid functional polyester available from PPG Industries, 35 acid value, 100% solids polyester resin
[4] PRIMID XL552 available from Ems
[5] Titanium dioxide
[6] Aluminium dioxide available from Aerox
[7] BaSO4 available from CIMBAR
[8] Resiflow PL 200 a flow agent available from Estron Chemical
[9] Benzoin available from Sigma Aldrich
[10] Licowax C available from Clariant Comparative Coating Composition 1

Comparative coating composition 1 is a polyester-based composition containing a thermoset resin (acid functional polyester available from PPG Industries, 35 acid value, 100% solids polyester resin), a crosslinker that reacts with acid groups, extender pigments and flow aids. Accordingly, comparative coating composition 1 contains thermoset resins only. The components were extruded via standard powder manufacturing methods and ground by standard methods.

The properties of the coatings were tested via the following methods. Results are shown in Table 2.

Test Methods

MEK rub test: The number of reciprocating rubs required to remove the coating was measured using a ball of cotton wool soaked in methyl ethyl ketone (MEK).

Blush test: Resistance to blush, which is white colouration of the film caused by water penetration and entrapment was measured by the following method. The coated panels were sterilised in an autoclave for 1 hour at 130° C. in a 1% solution of arylsulphosuccinate detergent in water and then the film was then observed visually.

Enamel rator: A 1 kg weight was dropped onto a coated panel from a 1 meter height to strike an indentation. The test was repeated two times under the same conditions on two individual cans. The integrity of the coating was measured using a WACO Enamel Rater Instrument and a 1% NaCl solution and reported in milliohms (mOhm).

Direct impact: Both tests use a Paul N Garnder Co. falling dart test on metal panels and references ASTM D 2794-93 test procedure. After the coating is impacted either directly or reverse impacted it is further subjected to Enamel Rator testing.

TABLE 2

Test Results

| | Coating Composition 1 | Comparative Coating Composition 1 |
|---|---|---|
| MEK double rubs | 100 | >100 |
| Blush | Pass-no blush | Pass-no blush |
| Enamel rater | <3 mOhms | <3 mOhms |
| Direct impact | >40 lbs | >40 lbs |
| Reverse impact | >40 lbs | >40 lbs |
| Adhesion | 5B | 5B |

The results show that the coating compositions according to the present invention perform as well, or better, than the coatings of the comparative examples.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A substrate coated on at least a portion thereof with a powder coating composition, the powder coating composition comprising:
    a thermoset resin comprising an acid functional polyester material;
    a thermoplastic resin; and
    a crosslinker,
    wherein the coating composition is substantially free of bisphenol A (BPA), bisphenol F (BPF), bisphenol A diglycidyl ether (BADGE) and bisphenol F diglycidyl ether (BFDGE).

2. The substrate of claim 1, wherein the acid functional polyester material is formed from a polyacid comprising succinic acid, glutaric acid, adipic acid, heptanoic acid, dodecanedioic acid or combinations thereof.

3. The substrate of claim 1, wherein the coating composition is substantially free of formaldehyde or sources thereof.

4. The substrate of claim 1, wherein the thermoplastic resin comprises epoxy resin, polyester resin, polyolefin resin, polyamide resin, polyurethane resin, polysiloxane resin, acrylic resin, and/or hydrocarbon resin.

5. The substrate of claim 1, wherein the crosslinker comprises a hydroxyalkylamide material, a hydroxyl functional alkyl polyurea material, and/or a carbodiimide resin.

6. The substrate of claim 1, wherein the substrate comprises metal, plastic, and/or laminate.

7. The substrate of claim 1, wherein the acid functional polyester material has an acid number of at least 25 mg KOH/g.

8. The substrate of claim 1, wherein the acid functional polyester material has a Tg of 50° C. to 100° C.

9. The substrate of claim 1, wherein the acid functional polyester material has a number average molecular weight of 1,000 to 20,000 Da.

10. The substrate of claim 1, wherein the acid functional polyester material has a weight average molecular weight of 5,000 to 20,000 Da.

11. The substrate of claim 1, wherein the acid functional polyester material has a melt viscosity at 200° C. of 10 to 50 Poise.

12. The substrate of claim 1, wherein the thermoplastic resin has a Tg of 40° C. to 80° C.

13. The substrate of claim 1, wherein the substrate forms at least a portion of a metal can, a plastic bottle, a plastic tube, a laminate, and/or flexible packaging.

14. The substrate of claim 1, wherein the substrate forms at least a portion of a monobloc aerosol can and/or tube.

15. The substrate of claim 1, wherein the substrate forms at least a portion of a food and/or beverage packaging.

16. The substrate of claim 1, wherein the acid functional polyester material comprises the reaction product of a polyacid and a polyol.

17. The substrate of claim 16, wherein the polyacid comprises at least 50 mol % terephthalic acid and/or isophthalic acid based on the total number of moles of polyacid.

18. The substrate of claim 16, wherein the polyol comprises at least 10 mol % of neopentyl glycol based on the total number of moles of polyol.

19. The substrate of claim 16, wherein the ratio of polyacid to polyol is from 20:1 to 1:20.

20. A packaging coated on at least a portion thereof with a powder coating composition, the powder coating composition comprising:
   a thermoset resin comprising an acid functional polyester material;
   a thermoplastic resin; and
   a crosslinker,
   wherein the coating composition is substantially free of bisphenol A (BPA), bisphenol F (BPF), bisphenol A diglycidyl ether (BADGE) and bisphenol F diglycidyl ether (BFDGE).

21. A method for producing a powder coating composition, the method comprising:
   extruding a polymer mixture comprising a thermoset resin comprising an acid functional polyester material, a thermoplastic resin, and a crosslinker to form a thermoset powder; and
   grinding the thermoset powder to an average particle size of 5 to 300 microns.

22. The method of claim 21, further comprising dry blending the polymer mixture before extruding.

* * * * *